United States Patent
Fessmann et al.

(10) Patent No.: US 7,285,136 B2
(45) Date of Patent: Oct. 23, 2007

(54) DIAMINOPYRAZOLE COMPOUNDS AND THE USE THEREOF IN THE OXIDATION DYEING OF KERATINOUS FIBRES

(75) Inventors: Thilo Fessmann, Aulnay Sous Bois (FR); Eric Terranova, Magagnose (FR)

(73) Assignee: L'Oreal, SA, Paris (FR)

( * ) Notice: Subject to any disclaimer, the term of this patent is extended or adjusted under 35 U.S.C. 154(b) by 0 days.

(21) Appl. No.: 10/468,288

(22) PCT Filed: Feb. 14, 2002

(86) PCT No.: PCT/FR02/00567

§ 371 (c)(1), (2), (4) Date: Dec. 3, 2003

(87) PCT Pub. No.: WO02/066441

PCT Pub. Date: Aug. 29, 2002

(65) Prior Publication Data

US 2004/0103487 A1 Jun. 3, 2004

(30) Foreign Application Priority Data

Feb. 21, 2001 (FR) .................................. 01 02310

(51) Int. Cl.
*A61K 7/13* (2006.01)

(52) U.S. Cl. .................. 8/405; 8/406; 8/408; 8/410; 8/421; 8/570; 8/573; 8/649; 8/670; 548/300

(58) Field of Classification Search ............... 8/405, 8/406, 408, 409, 410, 421, 570, 573, 649, 8/669, 670; 548/300
See application file for complete search history.

(56) References Cited

U.S. PATENT DOCUMENTS

| 4,823,985 | A | | 4/1989 | Grollier et al. ............... 222/1 |
|---|---|---|---|---|
| 5,032,137 | A | | 7/1991 | Junino et al. ................. 8/410 |
| 5,061,289 | A | * | 10/1991 | Clausen et al. ............... 8/405 |
| 5,663,366 | A | * | 9/1997 | Neunhoeffer et al. ..... 548/371.4 |
| 5,718,731 | A | * | 2/1998 | Loewe et al. .................. 8/409 |
| 2001/0009044 | A1 | | 7/2001 | Braun ........................... 8/409 |

FOREIGN PATENT DOCUMENTS

| DE | 38 43 892 | | 6/1990 |
|---|---|---|---|
| DE | 42 34 885 | | 4/1994 |
| DE | 196 43 059 | * | 4/1998 |
| DE | 196 46 609 | | 5/1998 |
| DE | 19646609 | * | 5/1998 |
| EP | 1166748 A2 | * | 1/2002 |
| FR | 2 586 913 | | 3/1987 |
| FR | 2 630 438 | | 10/1989 |

OTHER PUBLICATIONS

English abstract of the De Patent No. De 196 46 609 A1.*
STIC Search Report dated Nov. 17, 2006.*
English language Derwent Abstract of DE 196 46 609, May 14, 1998.

* cited by examiner

*Primary Examiner*—Eisa Elhilo
(74) *Attorney, Agent, or Firm*—Finnegan, Henderson, Farabow, Garrett, & Dunner, L.L.P.

(57) ABSTRACT

The invention relates to novel diaminopyrazole compounds having formula (I): wherein $R_1$ represents a linear or branched $C_4$-$C_5$ alkyl or n-propyl group, or a linear or branched $C_3$-$C_5$ mono or polyhydroxy alkyl group, and the addition salts thereof with a physiologically acceptable acid. The invention also relates to the compositions containing such a compound for the dyeing of keratinous fibres and the method for using said compositions.

26 Claims, No Drawings

DIAMINOPYRAZOLE COMPOUNDS AND THE USE THEREOF IN THE OXIDATION DYEING OF KERATINOUS FIBRES

The present invention relates to novel diaminopyrazole compounds, to a composition for the oxidation dyeing of keratin fibers, and in particular of human keratin fibers such as the hair, comprising at least one diaminopyrazole compound as oxidation base, and to the oxidation dyeing processes using it.

It is known practice to dye keratin fibers, and in particular human hair, with dye compositions containing oxidation dye precursors, in particular ortho- or para-phenylenediamines, ortho-aminophenols or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fiber, which may indeed be differently sensitized (i.e. damaged) between its tip and its root. They must also show good chemical stability in the formulations, and must have a good toxicological profile.

Furthermore, for a certain number of applications, dyes that produce chromatic shades on the hair are desired.

Patent applications DE 42 34 885 and 196 46 609 disclose 4,5-diaminopyrazole derivatives, which, when used together with various couplers, especially benzoxazines, give chestnut-brown shades with blue, red, violet, aubergine or coppery glints.

However, these dyes do not satisfy all the above requirements.

The Applicant has now discovered, entirely surprisingly and unexpectedly, that it is possible to obtain dyes, which are capable of producing powerful, particularly chromatic, bright and relatively unselective colorations, which have excellent properties of resistance to the various attacking factors to which keratin fibers may be subjected, by using as oxidation base the diaminopyrazoles of the formula (I) below or physiologically acceptable salts thereof.

One subject of the present invention is thus the novel diaminopyrazoles having the following structure (I):

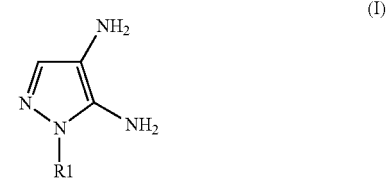

in which $R_1$ denotes a linear or branched $C_4$-$C_5$ n-propyl or alkyl group or a linear or branched $C_3$-$C_5$ mono- or polyhydroxyalkyl group.

A subject of the invention is also the physiologically acceptable acid salts of the compounds of formula (I), such as the hydrochlorides, hydrobromides, sulfates, tartrates, lactates or acetates.

$R_1$ preferably denotes a linear or branched n-propyl; butyl or pentyl group; a linear or branched propyl, butyl or pentyl group which is substituted by 1 to 4 OH radicals, depending on the possibilities of substitution of the groups mentioned above.

A subject of the invention is also a composition for the oxidation dyeing of keratin fibers, and in particular of human keratin fibers such as the hair, characterized in that it contains, in a medium that is suitable for dyeing, as oxidation base, at least one diaminopyrazole of formula (I) above, or acid salts thereof.

As mentioned above, the colorations obtained with the oxidation dye composition in accordance with the invention are powerful, particularly bright and chromatic. They in particular produce redder shades that are free of or contain very little blue or yellow. Furthermore, they show excellent properties of resistance with respect to the action of various external agents (light, bad weather, washing, permanent-waving, perspiration and friction).

A subject of the invention is also a process for the oxidation dyeing of keratin fibers using such a dye composition.

As examples of diaminopyrazoles of formula (I) according to the invention, mention may be made of the compounds belonging to the following classes:

| Structure | Name | Structure | Name | Structure | Name |
|---|---|---|---|---|---|
| ![structure] | 2-propyl-2H-pyrazole-3,4-diamine | ![structure] | 2-butyl-2H-pyrazole-3,4-diamine | ![structure] | 2-isobutyl-2H-pyrazole-3,4-diamine |

-continued

| Structure | Name | Structure | Name | Structure | Name |
|---|---|---|---|---|---|
| 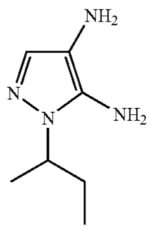 | 2-sec-butyl-2H-pyrazole-3,4-diamine | 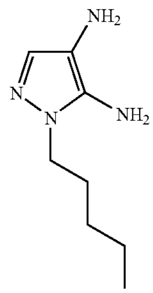 | 2-pentyl-2H-pyrazole-3,4-diamine | 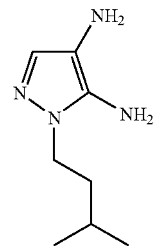 | 2-(3-methyl-butyl)-2H-pyrazole-3,4-diamine |
| 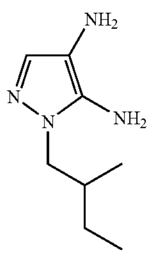 | 2-(2-methyl-butyl)-2H-pyrazole-3,4-diamine | 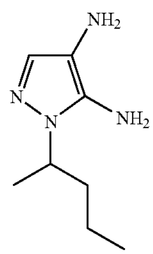 | 2-(1-methyl-butyl)-2H-pyrazole-3,4-diamine | 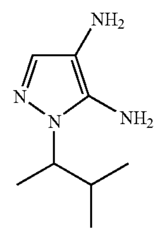 | 2-(1,2-dimethyl-propyl)-2H-pyrazole-3,4-diamine |
| 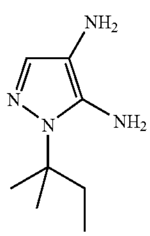 | 2-(1,1-dimethyl-propyl)-2H-pyrazole-3,4-diamine | 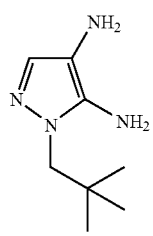 | 2-(2,2-dimethyl-propyl)-2H-pyrazole-3,4-diamine | 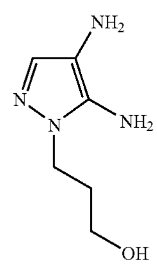 | 3-(4,5-diamino-pyrazol-1-yl)propan-1-ol |
| 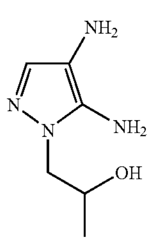 | 1-(4,5-diamino-pyrazol-1-yl)propan-2-ol | | | 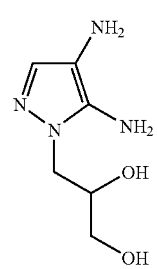 | 3-(4,5-diamino-pyrazol-1-yl)propane-1,2-diol |
| 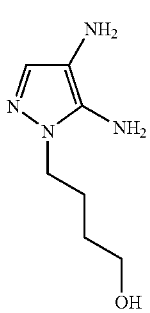 | 4-(4,5-diamino-pyrazol-1-yl)butan-1-ol | 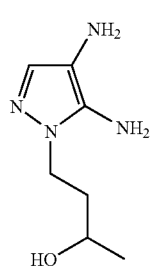 | 4-(4,5-diamino-pyrazol-1-yl)butan-2-ol | 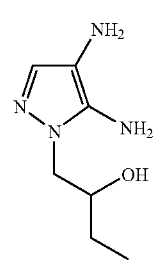 | 4-(4,5-diamino-pyrazol-1-yl)butan-3-ol |

-continued

| Structure | Name | Structure | Name | Structure | Name |
|---|---|---|---|---|---|
| 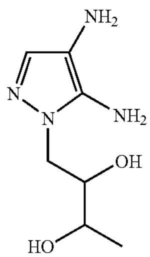 | 1-(4,5-diamino-pyrazol-1-yl)butane-2,3-diol | 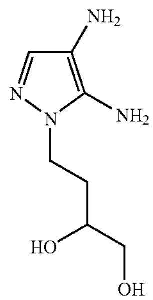 | 4-(4,5-diamino-pyrazol-1-yl)butane-1,2-diol | 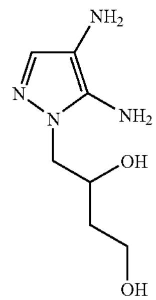 | 1-(4,5-diamino-pyrazol-1-yl)butane-2,4-diol |
| 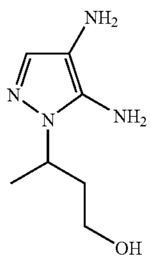 | 3-(4,5-diamino-pyrazol-1-yl)butan-1-ol | 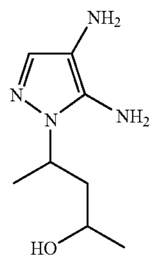 | 4-(4,5-diamino-pyrazol-1-yl)pentan-2-ol | 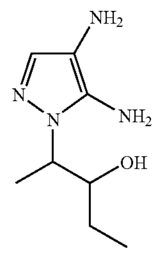 | 2-(4,5-diamino-pyrazol-1-yl)pentan-3-ol |
| 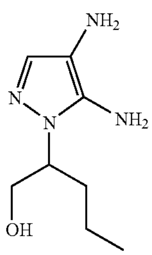 | 2-(4,5-diamino-pyrazol-1-yl)pentan-1-ol | 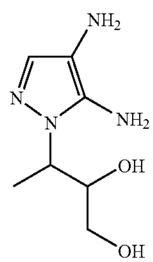 | 3-(4,5-diamino-pyrazol-1-yl)butane-1,2-diol | 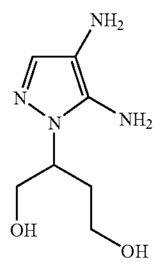 | 2-(4,5-diamino-pyrazol-1-yl)butane-1,4-diol |
| 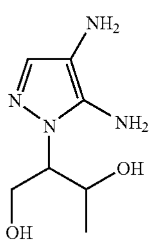 | 2-(4,5-diamino-pyrazol-1-yl)butane-1,3-diol | 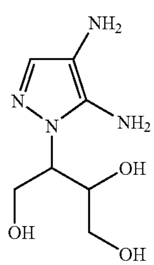 | 3-(4,5-diamino-pyrazol-1-yl)butane-1,2,4-triol | 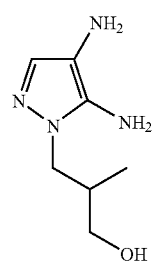 | 3-(4,5-diamino-pyrazol-1-yl)-2-methyl-propan-1-ol |
| 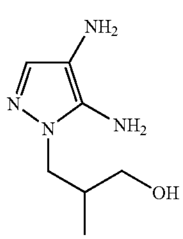 | 3-(4,5-diamino-pyrazol-1-yl)-2-methyl-propan-1-ol | 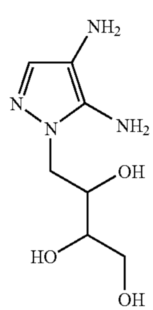 | 4-(4,5-diamino-pyrazol-1-yl)butane-1,2,3-triol | 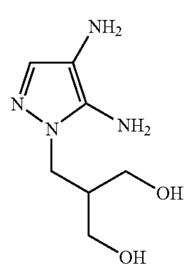 | 2-(4,5-diamino-pyrazol-1-ylmethyl)-propane-1,3-diol |

-continued

| Structure | Name | Structure | Name | Structure | Name |
|---|---|---|---|---|---|
| 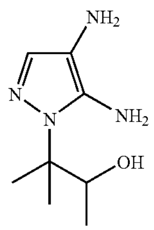 | 3-(4,5-diamino-pyrazol-1-yl)-3-methyl-butan-2-ol | 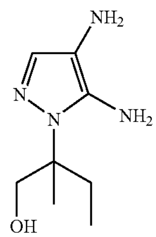 | 2-(4,5-diamino-pyrazol-1-yl)-2-methyl-butan-1-ol | 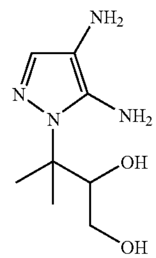 | 3-(4,5-diamino-pyrazol-1-yl)-3-methyl-butane-1,2-diol |
| 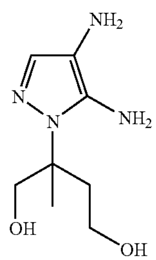 | 2-(4,5-diamino-pyrazol-1-yl)-2-methyl-butane-1,4-diol | 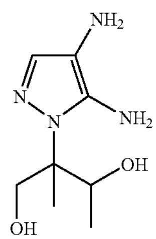 | 2-(4,5-diamino-pyrazol-1-yl)-2-methyl-pentane-1,3-diol | 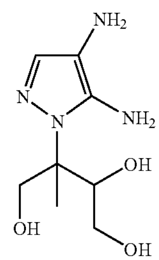 | 3-(4,5-diamino-pyrazol-1-yl)-3-methyl-butane-1,2,4-triol |
| 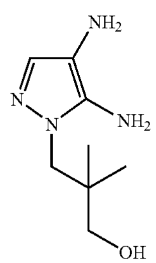 | 3-(4,5-diamino-pyrazol-1-yl)-2,2-dimethyl-propan-1-ol | 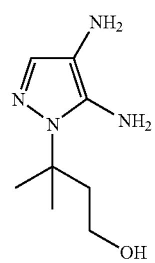 | 3-(4,5-diamino-pyrazol-1-yl)-3-methyl-butan-1-ol | 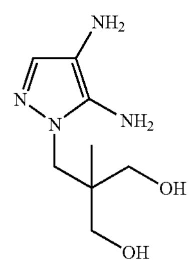 | 2-(4,5-diamino-pyrazol-1-ylmethyl)-2-methyl-propane-1,3-diol |
| 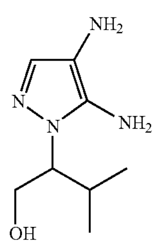 | 2-(4,5-diamino-pyrazol-1-yl)-3-methyl-butan-1-ol | 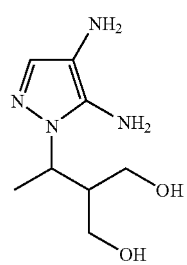 | 2-[1-(4,5-diamino-pyrazol-1-yl)ethyl]-propane-1,3-diol | 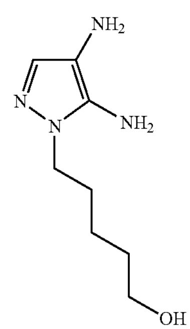 | 5-(4,5-diamino-pyrazol-1-yl)pentan-1-ol |
| 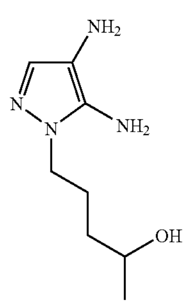 | 5-(4,5-diamino-pyrazol-1-yl)pentan-2-ol | 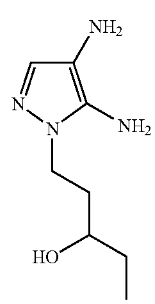 | 1-(4,5-diamino-pyrazol-1-yl)pentan-3-ol | 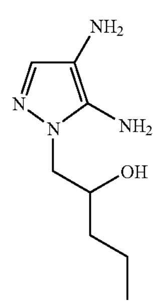 | 1-(4,5-diamino-pyrazol-1-yl)pentan-2-ol |

| Structure | Name | Structure | Name | Structure | Name |
|---|---|---|---|---|---|
| | 3-(4,5-diaminopyrazol-1-yl)-2-methyl-butan-1-ol | | 5-(4,5-diaminopyrazol-1-yl)pentane-1,2-diol | | 5-(4,5-diaminopyrazol-1-yl)pentane-1,3-diol |
| | 5-(4,5-diaminopyrazol-1-yl)pentane-1,4-diol | | 1-(4,5-diaminopyrazol-1-yl)pentane-2,3-diol | | 5-(4,5-diaminopyrazol-1-yl)pentane-2,3-diol |
| | 1-(4,5-diaminopyrazol-1-yl)pentane-2,4-diol | | 5-(4,5-diaminopyrazol-1-yl)pentane-1,2,3-triol | | 4-(4,5-diaminopyrazol-1-yl)pentan-1-ol |
| | 4-(4,5-diaminopyrazol-1-yl)pentan-2-ol | | 2-(4,5-diaminopyrazol-1-yl)pentan-3-ol | | 2-(4,5-diaminopyrazol-1-yl)pentan-1-ol |
| | 4-(4,5-diaminopyrazol-1-yl)pentane-1,2-diol | | 4-(4,5-diaminopyrazol-1-yl)pentane-1,2,3-triol | | 4-(4,5-diaminopyrazol-1-yl)pentane-1,2,3,5-tetraol |

| Structure | Name | Structure | Name | Structure | Name |
|---|---|---|---|---|---|
| 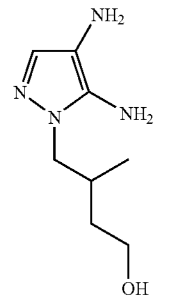 | 4-(4,5-diamino-pyrazol-1-yl)-3-methyl-butan-1-ol | 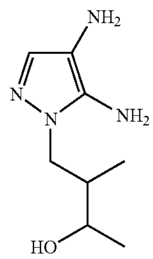 | 4-(4,5-diamino-pyrazol-1-yl)-3-methyl-butan-2-ol | 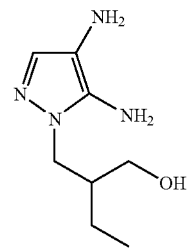 | 2-(4,5-diamino-pyrazol-1-ylmethyl)-butan-1-ol |
| 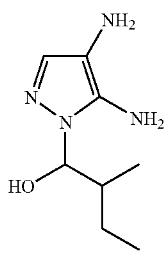 | 1-(4,5-diamino-pyrazol-1-yl)-2-methyl-butan-1-ol | 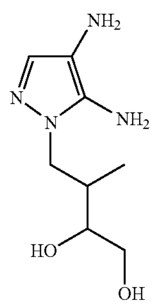 | 4-(4,5-diamino-pyrazol-1-yl)-3-methyl-butane-1,2-diol | 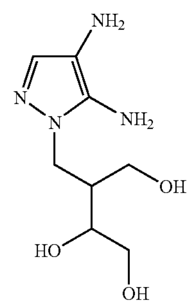 | 3-(4,5-diamino-pyrazol-1-ylmethyl)-butane-1,2,4-triol |
| 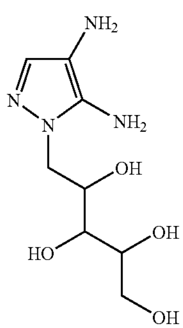 | 5-(4,5-diamino-pyrazol-1-yl)-pentane-1,2,3,4-tetraol | 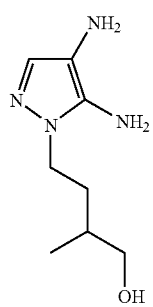 | 4-(4,5-diamino-pyrazol-1-yl)-2-methyl-butan-1-ol | 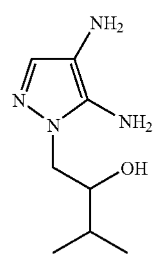 | 1-(4,5-diamino-pyrazol-1-yl)-3-methyl-butan-2-ol |
| 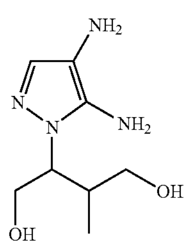 | 2-(4,5-diamino-pyrazol-1-yl)-3-methyl-butane-1,4-diol | 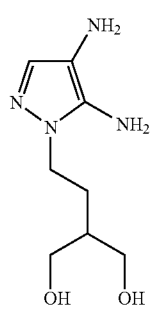 | 2-[2-(4,5-diamino-pyrazol-1-yl)ethyl]-propane-1,3-diol | 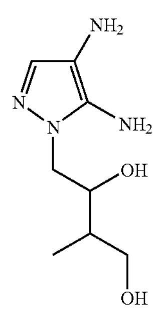 | 4-(4,5-diamino-pyrazol-1-yl)-2-methyl-butane-1,3-diol |
| | 4-(4,5-diamino-pyrazol-1-yl)-2-hydroxymethyl-butane-1,3-diol | | 2-(4,5-diamino-pyrazol-1-yl)-3-hydroxymethyl-butane-1,4-diol | | 3-(4,5-diamino-pyrazol-1-yl)-2-methyl-butan-1-ol |

| Structure | Name | Structure | Name | Structure | Name |
|---|---|---|---|---|---|
| 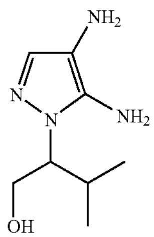 | 2-(4,5-diamino-pyrazol-1-yl)-3-methyl-butan-1-ol | 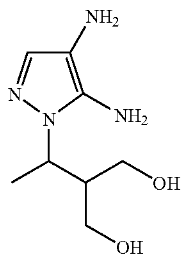 | 2-[1-(4,5-diamino-pyrazol-1-yl)ethyl]-propane-1,3-diol | 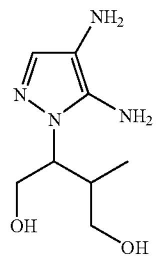 | 2-(4,5-diamino-pyrazol-1-yl)-3-methyl-butane-1,4-diol |

The diaminopyrazoles of formula (I) that are preferred according to the invention have the following structures:

| Structure | Name | Structure | Name | Structure | Name |
|---|---|---|---|---|---|
| 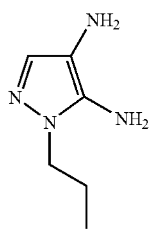 | 2-propyl-2H-pyrazole-3,4-diamine | 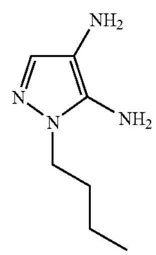 | 2-butyl-2H-pyrazole-3,4-diamine | 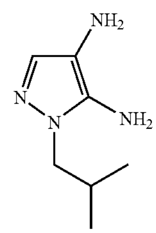 | 2-isobutyl-2H-pyrazole-3,4-diamine |
| 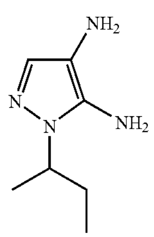 | 2-sec-butyl-2H-pyrazole-3,4-diamine | 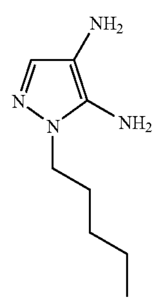 | 2-pentyl-2H-pyrazole-3,4-diamine | 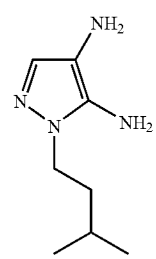 | 2-(3-methyl-butyl)-2H-pyrazole-3,4-diamine |
| 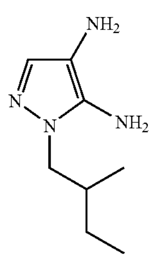 | 2-(2-methyl-butyl)-2H-pyrazole-3,4-diamine | 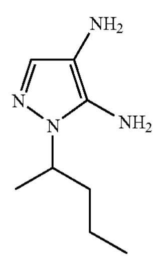 | 2-(1-methyl-butyl)-2H-pyrazole-3,4-diamine | 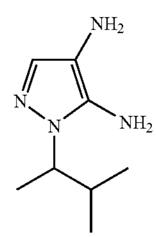 | 2-(1,2-dimethyl-propyl)-2H-pyrazole-3,4-diamine |
| 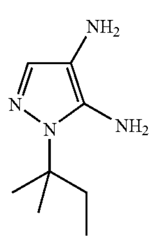 | 2-(1,1-dimethyl-propyl)-2H-pyrazole-3,4-diamine | 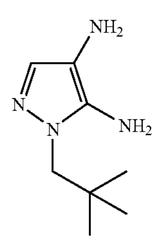 | 2-(2,2-dimethyl-propyl)-2H-pyrazole-3,4-diamine | 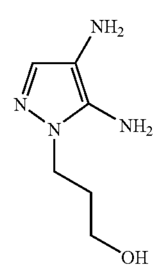 | 3-(4,5-diamino-pyrazol-1-yl)propan-1-ol |

-continued

| Structure | Name | Structure | Name | Structure | Name |
|---|---|---|---|---|---|
| 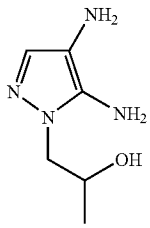 | 1-(4,5-diamino-pyrazol-1-yl)propan-2-ol | | | 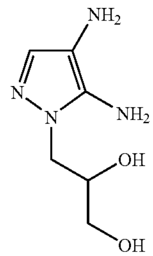 | 3-(4,5-diamino-pyrazol-1-yl)propane-1,2-diol |
| 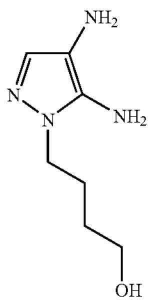 | 4-(4,5-diamino-pyrazol-1-yl)butan-1-ol | 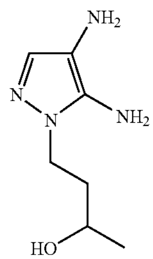 | 4-(4,5-diamino-pyrazol-1-yl)butan-2-ol | 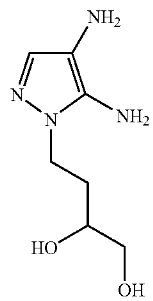 | 4-(4,5-diamino-pyrazol-1-yl)butane-1,2-diol |
| 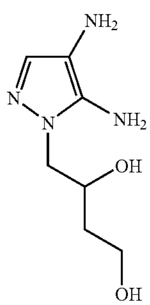 | 1-(4,5-diamino-pyrazol-1-yl)butane-2,4-diol | 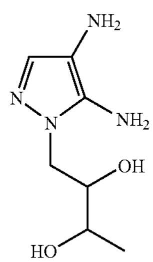 | 1-(4,5-diamino-pyrazol-1-yl)butane-2,3-diol | 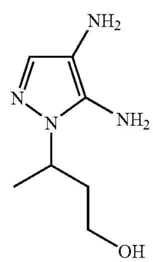 | 3-(4,5-diamino-pyrazol-1-yl)butan-1-ol |
| 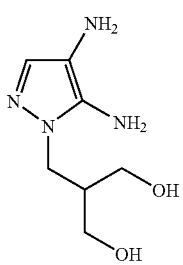 | 2-(4,5-diamino-pyrazol-1-ylmethyl)-propane-1,3-diol | | | 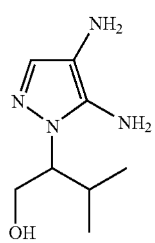 | 2-(4,5-diamino-pyrazol-1-yl)-3-methyl-butan-1-ol |
| 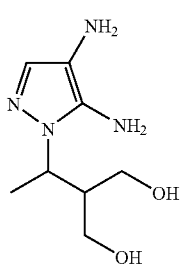 | 2-[1-(4,5-diamino-pyrazol-1-yl)ethyl]-propane-1,3-diol | 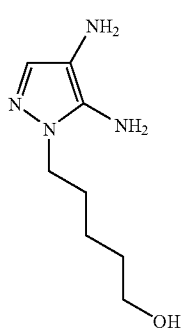 | 5-(4,5-diamino-pyrazol-1-yl)pentan-1-ol | 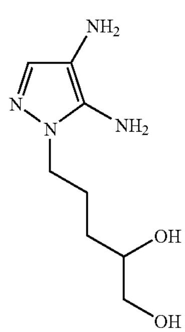 | 5-(4,5-diamino-pyrazol-1-yl)pentane-1,2-diol |

| Structure | Name | Structure | Name | Structure | Name |
|---|---|---|---|---|---|
| | 5-(4,5-diaminopyrazol-1-yl)pentane-1,3-diol | | 5-(4,5-diaminopyrazol-1-yl)pentane-1,4-diol | | 5-(4,5-diaminopyrazol-1-yl)pentane-2,3-diol |
| | 1-(4,5-diaminopyrazol-1-yl)pentane-2,4-diol | | 1-(4,5-diaminopyrazol-1-yl)pentane-2,3-diol | | |
| | 4-(4,5-diaminopyrazol-1-yl)pentan-1-ol | | 4-(4,5-diaminopyrazol-1-yl)-3-methyl-butane-1,2-diol | | 2-[2-(4,5-diaminopyrazol-1-yl)ethyl]-propane-1,3-diol |
| | 3-(4,5-diaminopyrazol-1-yl)-2-methyl-butan-1-ol | | 3-(4,5-diaminopyrazol-1-yl)propan-1-ol | | |

The diaminopyrazoles of formula (I) that are more particularly preferred according to the invention are
2-propyl-2H-pyrazole-3,4-diamine
2-isobutyl-2H-pyrazole-3,4-diamine
2-(2,2-dimethylpropyl)-2H-pyrazole-3,4-diamine
3-(4,5-diaminopyrazol-1-yl)propan-1-ol
1-(4,5-diaminopyrazol-1-yl)propan-2-ol
3-(4,5-diaminopyrazol-1-yl)propane-1,2-diol
4-(4,5-diaminopyrazol-1-yl)butan-1-ol
4-(4,5-diaminopyrazol-1-yl)butane-1,2-diol
5-(4,5-diaminopyrazol-1-yl)pentan-1-ol or the addition physiologically acceptable acid salts thereof.

The diaminopyrazoles of formula (I) according to the invention are prepared, for example, according to the following general preparation method:

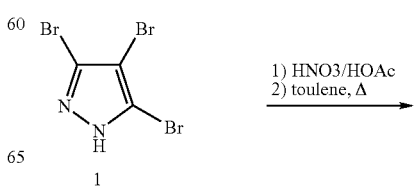

-continued

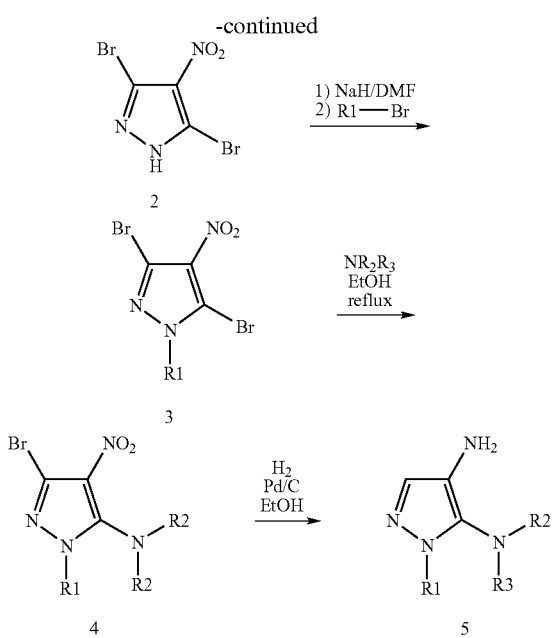

The synthetic approach shown below is described in the literature up to intermediate (2) (J. H. P. Juffermanns, C. L.; Habraken; J. Org. Chem., 1986, 51, 4656; Klebe et al., Synthesis, 1973, 294; R. Hüttel, F. Buchele; Chem. Ber., 1955, 88, 1586). The alkylation and the amination to obtain the compounds of the type (5) of formula (I) according to the invention are mentioned, for example, in document DE 42 34 885.

The dye composition according to the invention especially contains from 0.001% to 10% by weight, preferably from 0.05% to 6% by weight and even more preferably from 0.1% to 3% by weight of at least one diaminopyrazole of formula (I) or of the salts thereof.

The dye composition in accordance with the invention may also contain, in addition to the diaminopyrazole(s) defined above, at least one additional oxidation base that may be chosen from the oxidation bases conventionally used in oxidation dyeing and among which mention may be made especially of para-phenylenediamines, bis(phenyl)alkylenediamines, para-aminophenols, ortho-aminophenols and heterocyclic bases other than the 4,5-diaminopyrazoles used in accordance with the invention.

Among the para-phenylenediamines that may be mentioned more particularly, for example, are para-phenylenediamine, para-tolylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline and the para-phenylenediamines described in French patent application FR 2 630 438, and the addition salts thereof.

Among the bis(phenyl)alkylenediamines that may be mentioned more particularly, for example, are N,N'-bis(β-hydroxyethyl)-N,N'-bis(4'-aminophenyl)-1,3-diamino-propanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof.

Among the heterocyclic bases that may be mentioned more particularly, for example, are pyridine derivatives, pyrimidine derivatives, pyrazole derivatives other than the diaminopyrazoles of formula (I) used in accordance with the invention, and the addition salts thereof.

When they are used, these additional oxidation bases preferably represent from 0.0005% to 12% by weight relative to the total weight of the dye composition and even more preferably from 0.005% to 6% by weight relative this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, meta-aminophenols, meta-diphenols, mono- or polyhydroxylated naphthalene derivatives and heterocyclic couplers such as, for example, indole or pyridine derivatives, and the addition salts thereof.

These couplers are chosen more particularly from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino) toluene, and the addition salts thereof.

When they are present, these couplers especially represent from 0.0001% to 10% of the total weight of the dye composition, preferably from 0.005% to 5% by weight and even more preferably from 0.1% to 3% of this weight.

In general, the addition salts with an acid that may be used in the context of the dye compositions of the invention (oxidation bases and couplers) are chosen especially from the hydrochlorides, hydrobromides, sulfates, tartrates, lactates and acetates. The addition salts with a base are especially those obtained with sodium hydroxide, potassium hydroxide, ammonia, amines or alkanolamines.

The medium that is suitable for dyeing (or support) used according to the invention consists of water or of a mixture of water and at least one organic solvent chosen from $C_1$-$C_4$ lower alkanols, polyols and polyol ethers, aromatic alcohols, similar products and mixtures thereof.

The dye composition according to the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, reducing agents, sunscreens, penetrating agents, sequestering agents, fragrances, buffers, dispersants, conditioners, for instance silicones, film-forming agents, preserving agents and opacifiers.

The pH of the dye composition according to the invention is between 3 and 12.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibers, and especially human hair.

Another subject of the invention is a process for dyeing keratin fibers, and in particular human keratin fibers such as the hair, using the dye composition as defined above.

According to this process, at least one dye composition as defined above is applied to the fibers, for a time that is sufficient to develop the desired coloration, either in air or using an oxidizing agent. The dye composition may optionally contain oxidation catalysts, so as to accelerate the oxidation process.

According to a first embodiment of the process of the invention, the coloration of the fibers may be performed without adding an oxidizing agent, solely by contact with atmospheric oxygen.

According to a second embodiment of the process of the invention, at least one dye composition as defined above is applied to the fibers, the color being revealed at acidic, neutral or alkaline pH using an oxidizing agent that is added to the composition just at the time of use, or which is present in an oxidizing composition applied simultaneously or sequentially in a separate manner.

According to this second embodiment of the dyeing process of the invention, the dye composition described above is preferably mixed, at the time of use, with an oxidizing composition containing, in a medium that is suitable for dyeing, at least one oxidizing agent present in an amount that is sufficient to develop a coloration. The mixture obtained is than applied to the keratin fibers and is left for an action time of 3 to 50 minutes and preferably 5 to 30 minutes, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulfates. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12, and even more preferably between 5 and 11. It is adjusted to the desired value by means of acidifying or basifying agents usually used in the dyeing of keratin fibers, and as defined above.

The oxidizing composition as defined above may also contain various adjuvants conventionally used in compositions for dyeing the hair and as defined above.

The composition that is finally applied to the keratin fibers may be in various forms, such as in the form of liquids, creams or gels, or in any other form that is suitable for dyeing keratin fibers, and especially human hair.

Another subject of the invention is a multi-compartment device or dyeing "kit" or any other multi-compartment packaging system, a first compartment of which contains the dye composition as defined above, and a second compartment of which contains the oxidizing composition as defined above. These devices may be equipped with a means for applying the desired mixture to the hair, such as the devices described in patent FR-2 586 913 in the name of the Applicant.

The examples that follow are intended to illustrate the invention without, however, limiting its scope.

EXAMPLES

Examples of Synthesis of Compounds of Formula
(I)

Synthesis of 3,4,5-tribromopyrazole (1):

An aqueous solution (350 ml) containing sodium hydroxide (24 g, 0.6 mol) and pyrazole (10 g, 0.147 mol) was prepared with stirring. After cooling the reaction medium to 20° C., $Br_2$ (72 g, 0.45 mol) was added dropwise over 1 hour, while maintaining the temperature between 20° C. and 25° C. The reaction was monitored by thin layer chromatography (TLC) (50% hexane/50% EtOAc or ethyl acetate). The precipitate was filtered off and washed with demineralized water (100 ml). The filtrate was acidified to pH 6-7 using HCl (10%, 33 g, 0.27 mol) and maintaining the temperature between 20 and 25° C. The precipitate thus formed was filtered off and washed with demineralized water (100 ml). The combined solids were maintained at reflux in Dean-Stark apparatus in the presence of toluene (200 ml). At the end of collection of the water, the organic phase was filtered while hot. The solvent was evaporated down to a residual volume of 110 ml. The solution was cooled to 0-5° C. for 1 hour. The precipitate formed was collected by filtration, washed with cold toluene (20 ml) and dried under vacuum at 80° C. to give the 3,4,5-tribromopyrazole (1) in the form of an off-white solid (30 g, 67%).

$^{13}C$ NMR (100 MHz, $d_6$-DMSO): 97.7, 116.1, 126.4 melting point: 182-184° C.

Synthesis of 3,5-dibromo-4-nitropyrazole (2):

$HNO_3$ (d=1.50 g/ml; 18 ml, 0.429 mol) was added dropwise over 10 minutes to a solution of 3,4,5-tribromopyrazole (1) (50 g, 0.164 mol) in glacial acetic acid (750 ml) while maintaining the temperature at 15° C. Acetic anhydride (250 ml) was added and the reaction mixture was stirred at room temperature for 2 hours. Once the reaction was complete, the reaction mixture was poured onto crushed ice (1 kg). After stirring for 1 hour, the crude product was filtered off and then washed with demineralized water (2×60 ml) to give crude 1-nitro-3,4,5-tribromopyrazole. The water (24.6 ml) contained in the wet product was removed by heating a solution of the product in toluene (750 ml) at reflux in Dean-Stark apparatus. The toluene solution was maintained at reflux for a further 30 minutes until a TLC (eluent: toluene) showed that the rearrangement of the 1-nitro-3,4,5-tribromopyrazole (Rf=0.77), the intermediate formed, into 3,5-dibromo-4-nitropyrazole 2 (Rf=0.05) was complete. The solution was concentrated to a residual volume of 150 ml and then allowed to cool to 60° C., followed by addition of hexane (275 ml). The solution was cooled to 0-5° C. for 1 hour and the 3,5-dibromo-4-nitropyrazole (2) (29.1 g, 65%) was recovered by filtration and drying under vacuum in the form of a pale yellow solid.

melting point: 127.6-130.1° C.

Synthesis of 3-(3,5-dibromo-4-nitropyrazol-1-yl)propan-1-ol (3-1):

A mixture of 3,5-dibromo-4-nitropyrazole (2) (2.0 g; 7.38 mmol) in DMF (9.5 ml) was added over 15 minutes to a suspension of NaH (0.32 g, 8.0 mmol; 60% dispersion in oil, prewashed with hexane) in DMF (16 ml) with stirring and under an inert atmosphere. After stirring for 15 minutes, a solution of 3-bromo-1-propanol (1.0 g; 7.19 mmol) in DMF (3.2 ml) was added dropwise. The reaction mixture was heated at 80° C. for 2 hours (monitored by TLC) and the DMF was then evaporated off under reduced pressure. A mixture of DCM/water (20 ml, 1/1) was added. The organic phase was dried over $Na_2SO_4$ and the solvent was evaporated off under reduced pressure. The crude reaction product was obtained as a black oil (1.9 g, 79%), which was used without further purification in the amination step.

Synthesis of 1-propyl-3,5-dibromo-4-nitropyrazole (3-2):

A mixture of 3,5-dibromo-4-nitropyrazole (2) (25 g, 92 mmol) in DMF (120 ml) was added over 45 minutes to a suspension of NaH (4.0 g, 10 mmol; 60% dispersion in oil, prewashed with hexane) in DMF (200 ml) with stirring and under an inert atmosphere. After stirring for 30 minutes, a solution of 1-bromopropane (13.6 g, 111 mmol) in DMF (40 ml) was added over 10 minutes. The reaction mixture was heated at 50-60° C. for 3 hours (monitored by TLC) and the DMF was then evaporated off under reduced pressure. A mixture of DCM/water (300 ml, 1/5) was added and the organic phase was then extracted with water (2×50 ml). The organic phase was dried over $Na_2SO_4$ and the solvent was evaporated off under reduced pressure. The crude reaction product was obtained as a black oil (19.4 g, 70%), which was used without further purification in the amination step.

Synthesis of 1-(3,5-dibromo-4-nitropyrazol-1-yl)propan-2-ol (3-3):

A mixture of 3,5-dibromo-4-nitropyrazole (2) (40.0 g; 147 mmol) in DMF (200 ml) was added over 15 minutes to a suspension of NaH (6.5 g, 162 mmol; 60% dispersion in oil, prewashed with hexane) in DMF (320 ml) with stirring and under an inert atmosphere. After stirring for 35 minutes, a solution of 1-bromo-2-propanol (26.8 ml; 221 mmol) in DMF (80 ml) was added dropwise. The reaction mixture was heated at 80° C. for 2 hours and the DMF was then evaporated off under reduced pressure. A mixture of DCM/water (480 ml, 2/1) was added. The organic phase was extracted with DCM (2×160 ml). The combined organic phases were washed with water (3×400 ml). The organic phase was dried over $Na_2SO_4$ and the solvent was evaporated off under reduced pressure. The 1-(3,5-dibromo-4-nitropyrazol-1-yl)-propan-2-ol was obtained as a white solid (23.3 g; 48%).

$R_f$ (DCM/MeOH: 95/5)=0.8

00 MHz, $d^6$-DMSO): 5.10 (1H, d, OH), 4.22-4.02 (3H, $m_{broad}$, $CH_2CH$ and $CH_2CH$), 1.15 (3H, d, $CH_3$).

Synthesis of 3-(3,5-dibromo-4-nitropyrazol-1-yl)-propane-1,2-diol (3-4):

A mixture of 3,5-dibromo-4-nitropyrazole (2) (40.0 g; 147 mmol) in DMF (200 ml) was added over 15 minutes to a suspension of NaH (6.5 g, 162 mmol; 60% dispersion in oil, prewashed with hexane) in DMF (320 ml) with stirring and under an inert atmosphere. After stirring for 30 minutes, a solution of 3-bromo-1,2-propanediol (19.4 ml; 221 mmol) in DMF (80 ml) was added dropwise. The reaction mixture was heated at 80° C. for 3 hours and the DMF was then evaporated off under reduced pressure. A mixture of DCM/water (480 ml, 2/1) was added. A yellow solid precipitated out. After washing with ether (50 ml), the 3-(3,5-dibromo-4-nitropyrazol-1-yl)-propane-1,2-diol (32.3 g, 63%) was obtained as a white solid (23.3 g; 48%).

$R_f$ (DCM/MeOH: 90/10)=0.35

$^1H$ NMR (200 MHz, $d^6$-DMSO): 5.09 (1H, d, CHOH), 4.80-4.75 (1H, $t_{broad}$, $CH_2OH$), 4.27-4.15 (2H, m, $CH_2OH$), 3.35-3.29 (3H, m, N—$CH_2CH$ and $CH_2CH$).

Synthesis of 3-(5-benzylamino-3-bromo-4-nitropyrazol-1-yl)propan-1-ol (4-1):

A mixture of 3-(3,5-dibromo-4-nitropyrazol-1-yl)propan-1-ol (3-2) (17.1 g, 52 mmol), EtOH (100 ml) and benzylamine (27.9 g, 260 mmol) was refluxed for 15 hours. The reaction medium was concentrated to the maximum under reduced pressure. The highly viscous residue was suspended in EtOAc (100 ml) and EtOH (100 ml). The organic phase was washed with NaCl solution (10%, 100 ml) and then dried over $Na_2SO_4$. After evaporating off the solvent under reduced pressure, an orange-colored oil was obtained (13.6 g), which was subsequently purified by column chromatography (gradient: 10%/90% EtOAc/hexane to 40%/60% EtOAc/hexane) in order to obtain, after evaporating off the solvent, the 3-(5-benzylamino-3-bromo-4-nitropyrazol-1-yl)propan-1-ol in the form of a yellow solid (8.8 g, 48%).

melting point: 95.0-96.5° C.

$^1H$ NMR (400 MHz, $CDCl_3$): 7.40-7.30 (5H, m, $H_{Ar}$); 4.68 (2H, d, J=7.0 Hz, $NHCH_2$), 4.16 (2H, t, J=7.0 Hz, $CH_2N$), 3.65 (2H, t, J=7.0 Hz, $CH_2O$); 2.02 (2H, m, $CH_2CH_2CH_2$).

Synthesis of benzyl(5-bromo-4-nitro-2-propyl-2H-pyrazol-3-yl)amine (4-2):

A mixture of 1-propyl-3,5-dibromo-4-nitropyrazole (19.4 g, 62 mmol), EtOH (500 ml) and benzylamine (40 g, 373 mmol) was refluxed for 15 hours. The reaction medium was concentrated to the maximum under reduced pressure. The residue was suspended in EtOAc (100 ml), the insoluble part was separated out by filtration and the filtrate was evaporated to dryness. The black oil obtained was purified by column chromatography (eluent: EtOAc/hexane) to give the benzyl(5-bromo-4-nitro-2-propyl-2H-pyrazol-3-yl) amine in the form of a yellow solid (9 g; 29%) from 3,5-dibromo-4-nitropyrazole.

melting point: 91.8-92.3° C.

$^1H$ NMR (400 MHz, $CDCl_3$): 7.41-7.31 (5H, m, $H_{arom}$); 4.61 (2H, d, J=6.5 Hz, $NHCH_2$), 3.94 (2H, t, J=7.5 Hz, $CH_2N$), 1.83 (2H, m, $CH_3CH_2$), 0.89 (3H, t, J=7.5 Hz, $CH_3$).

Synthesis of 1-(5-benzylamino-3-bromo-4-nitropyrazol-1-yl)propan-2-ol (4-3):

A mixture of 1-(3,5-dibromo-4-nitropyrazol-1-yl)propan-2-ol (3-3) (22 g, 666 mmol), EtOH (300 ml) and benzylamine (102 g, 936 mmol) was refluxed for 1.5 hours. The reaction medium was concentrated to the maximum under reduced pressure. DCM (100 ml) was added to the residue. The organic phase was washed with dilute acid (5×50 ml).

The organic phase was dried over Na₂SO₄ and the solvent was evaporated off under reduced pressure. The brown oil obtained was treated with diisopropyl ether at 0° C. to give the 1-(5-benzylamino-3-bromo-4-nitropyrazol-1-yl)propan-2-ol (13.7 g, 58%) in the form of a yellow solid.

melting point: 81.3° C.

m/z (ES⁺): 355 [M+H]⁺; 377 [M+Na]⁺; 733 [2M+Na]⁺.

Synthesis of 3-(5-benzylamino-3-bromo-4-nitropyrazol-1-yl)propane-1,2-diol (4-4):

A mixture of 1-(3,5-dibromo-4-nitropyrazol-1-yl)-propane-1,2-diol (3-4) (31 g, 898 mmol), EtOH (420 ml) and benzylamine (138 g, 1.26 mol) was refluxed for 1.5 hours. The reaction medium was concentrated to the maximum under reduced pressure. 100 ml of DCM were added to the residue. The organic phase was washed with dilute acid (5×50 ml). The organic phase was dried over Na₂SO₄ and the solvent was evaporated off under reduced pressure. The brown oil obtained was treated with diisopropyl ether at 0° C. to give the 3-(5-benzylamino-3-bromo-4-nitropyrazol-1-yl)propane-1,2-diol (14.1 g, 42%) in the form of a yellow solid.

melting point: 90.1° C.

m/z (ES⁺): 372 [M+H]⁺; 395 [M+Na]⁺; 767 [2M+Na]⁺.

Synthesis of 3-(4,5-diaminopyrazol-1-yl)propan-1-ol hydrobromide and hydrochloride (5-1):

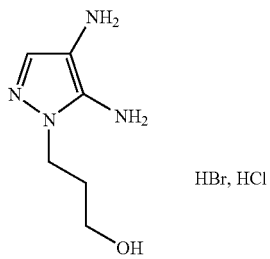

A mixture of 3-(5-benzylamino-3-bromo-4-nitropyrazol-1-yl)propan-1-ol (4-1) (8.8 g; 24.8 mmol) in EtOH (500 ml) containing 10% Pd/C as catalyst (Johnson-Mattey Type 487, 0.9 g dry weight) and 36% hydrochloric acid (6.0 g, 59 mmol) was hydrogenated in an autoclave (1 l) at 11 bar for 5 hours. The catalyst was filtered off and washed with EtOH, and the filtrate was evaporated under reduced pressure. Under an inert atmosphere, the crude oil was taken up in EtOH (50 ml) and heated to 50° C. EtOAc (50 ml) was added and the mixture was cooled first to room temperature and then to 0-5° C. over 2 hours. The precipitate formed was recovered by filtration, washed with a cold mixture of EtOH/EtOAc (1/1, 2×30 ml) and dried under vacuum to give the 3-(4,5-diaminopyrazol-1-yl)propan-1-ol in the form of the hydrobromide and hydrochloride (1.06 eq HBr and 0.94 eq HCl) as an off-white solid (2.4 g, 42%).

melting point: 275-280° C.

elemental analysis: C₈H₁₄N₄O (1.06 HBr, 0.94 HCl)

found: C: 26.13%, H: 5.13%, N: 20.09%, O: 5.92%, Br: 29.05%, Cl: 12.60% theory: C: 26.34%, H: 5.16%, N: 20.48%, 0: 5.85%, Br: 29.21%, Cl: 12.96%

¹H NMR (400 MHz, d⁶-DMSO): 8.26 (1H, s, H$_{py}$); 5.18 (1H, s$_{broad}$, NH), 4.02 (2H, m, CH₂N), 3.45 (2H, m, CH₂O), 1.85 (2H, m, CH₂)

Synthesis of 4,5-diamino-1-propylpyrazole hydrobromide and hydrochloride (5-2):

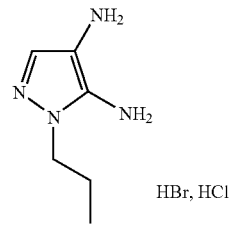

A mixture of benzyl (5-bromo-4-nitro-2-propyl-2H-pyrazol-3-yl)amine (7 g; 21 mmol) in EtOH (500 ml) containing 10% Pd/C as catalyst (Johnson-Mattey Type 487, 0.5 g dry weight) and 36% hydrochloric acid (5.0 g, 49 mmol) was hydrogenated in a Parr autoclave (1 l) at 11 bar for 3 hours. The catalyst was filtered off and washed with EtOH, and the filtrate was evaporated under reduced pressure. Under an inert atmosphere, the crude orange oil was taken up in EtOH and heated to 40° C. EtOAc (90 ml) was added and the mixture was maintained at room temperature for 15 hours. The precipitate formed was recovered by filtration, washed with a cold mixture of EtOH/EtOAc (1/1, 2×20 ml) and dried under vacuum to give the 4,5-diamino-1-propylpyrazole in the form of the hydrobromide hydrochloride (0.55 eq HBr and 1.38 eq HCl) as an off-white solid (2.5 g, 57%).

melting point: 168.1-173.0° C.

elemental analysis: C₆H₁₂N₄ (0.55 HBr, 1.38 HCl)

found: C: 29.08%, H: 6.06%, N: 22.87% theory: C: 27.98%, H: 5.48%, N: 21.75%

¹H NMR (400 MHz, d⁶-DMSO): 7.34 (1H, s, H$_{py}$); 5.18 (1H, s$_{broad}$, NH); 4.09 (2H, t, J=5.5 Hz, CH₂N); 3.61 (2H, t, J=5.5 Hz, CH₂O); 3.23 (3H, s, OCH₃).

Synthesis of 1-(4,5-diaminopyrazol-1-yl)propan-2-ol hydrobromide (5-3):

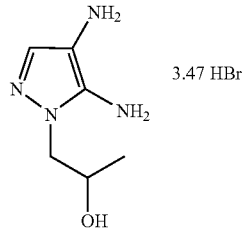

A mixture of 1-(5-benzylamino-3-bromo-4-nitropyrazol-1-yl)propan-2-ol (4-3) (5.0 g; 14.0 mmol) in EtOH (140 ml) containing 10% Pd/C as catalyst (Engelhard, 50% wet, 0.5 g dry weight) and NaOH (solid, 560 mg, 14 mmol) was hydrogenated in an autoclave (1 l) at 11 bar for 2 hours. The reaction mixture was filtered to remove the catalyst, under an inert atmosphere in an ethanolic solution containing HBr (47%, 9.7 ml, 78 mmol). The solvent was evaporated off under reduced pressure to give a solid. After washing with cold EtOH, the 1-(4,5-diaminopyrazol-1-yl)propan-2-ol was obtained in the form of the hydrobromide (3.47 eq HBr) as a white solid (2.3 g, 42%).

melting point: 222.3° C.

elemental analysis: C₆H₁₂N₄O (3.47 HBr)

found: C: 15.75%, H: 3.03%, N: 11.54%, O: 4.15%, Br: 59.26% theory: C: 15.02%, H: 3.36%, N: 11.68%, O: 3.33%, Br: 66.61%

$^1$H NMR (400 MHz, d$^6$-DMSO): 7.72 (1H, s, CH$_{arom}$); 7.66-6.20 (7 h, S$_{broad}$, NH$_2$ and OH and HBr); 4.23-4.07 (3H, m, NCH$_2$CH and NCH$_2$CH); 1.29 (3H, d, CH$_3$).

Synthesis of 3-(4,5-diaminopyrazol-1-yl)propane-1,2-diol hydrobromide (5-4):

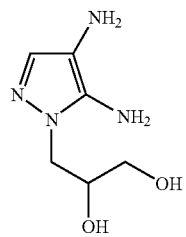

A mixture of 3-(5-benzylamino-3-bromo-4-nitropyrazol-1-yl)propane-1,2-diol (4-4) (7.0 g; 18.8 mmol) in EtOH (150 ml) containing 10% Pd/C as catalyst (Engelhard, 50% wet, 0.7 g dry weight) and NaOH (solid, 800 mg, 18.8 mmol) was hydrogenated in an autoclave (1 l) at 16 bar for 3.5 hours. The reaction mixture was filtered to remove the catalyst under an inert atmosphere, in an ethanolic solution containing HBr (47%, 7.1 ml, 57 mmol). The solvent was evaporated off under reduced pressure to give a solid. After washing with cold EtOH, the 3-(4,5-diaminopyrazol-1-yl)propane-1,2-diol hydrobromide was obtained as an off-white solid.

$^1$H NMR (400 MHz, d$^6$-DMSO): 7.90 (1H, s, H$_{arom}$); 4.30-4.14 (3H, m, NCH$_2$CH and NCH$_2$CH); 3.69-3.60 (2H, m, CH$_2$OH).

Formulation Examples in Alkaline Medium

The dye formulations below are prepared:

| | |
|---|---|
| 4, 5-diaminopyrazole of formula (I) | 5 × 10$^{-3}$ mol |
| coupler | 5 × 10$^{-3}$ mol |
| oleyl alcohol polyglycerolated with 2 mol of glycerol | 4.0 g |
| oleyl alcohol polyglycerolated with 4 mol of glycerol, containing 78% active material (A.M.) | 5.7 g A.M. |
| oleic acid | 3.0 g |
| oleylamine containing 2 mol of ethylene oxide, sold under the trade name Ethomeen O12 by the company Akzo | 7.0 g |
| diethylaminopropyl laurylamino succinamate, sodium salt, at 55% A.M. | 3.0 g A.M. |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite as an aqueous solution containing 35% A.M. | 0.455 g A.M. |
| ammonium acetate | 0.8 g |
| antioxidant, sequestering agent | qs |
| fragrance, preserving agent | qs |
| aqueous ammonia containing 20% NH$_3$ | 10 g |

The pH of the composition is 9.5
A.M. means "active mateial"

| Examples | Base | Coupler |
|---|---|---|
| 1 | 3-(4-,5 diaminopyrazol-1-yl)propan-1-ol, 1.06 HBr, 0.94 HCl (5-1) | 5-amino-6-chloro-2-methylphenol |
| 2 | 3-(4-,5 diaminopyrazol-1-yl)propan-1-ol 1.06 HBr, 0.94 HCl (5-1) | 1 β-hydroxyethoxy-2,4-diaminobenzene, 2 HCl |
| 3 | 2-propyl-2H-pyrazole-3,4-diamine 0.55 HBr, 1.38 HCl (5-2) | 5-amino-6-chloro-2-methylphenol |
| 4 | 2-propyl-2H-pyrazole-3,4-diamine 0.55 HBr, 1.38 HCl (5-2) | 1 β-hydroxyethoxy-2,4-diaminobenzene, 2 HCl |

At the time of use, each dye composition is mixed, weight for weight, with a 20-volumes aqueous hydrogen peroxide solution (6% by weight), the pH of which has been adjusted to about 2.5 with orthophosphoric acid.

The mixture is applied to natural or permanent-waved grey hair containing 90% white hairs, at a rate of 5 g per 0.5 g of hair, for 30 minutes.

The hair is then rinsed, washed with a standard shampoo and dried.

The color of the locks was evaluated in the L*a*b* system, on white and permanent-waved hair, using a Minolta CM 2002 spectrophotometer.

In the L*a*b* space, the lightness is indicated by the value L* on a scale from 0 to 100, while the chromatic data is expressed by a* and b* which indicate two color axes, a* the red-green axis and b* the yellow-blue axis.

According to this system, the higher the value of L, the paler and less intense the color. Conversely, the lower the value of L, the darker or more intense the color.

| | Natural white hair | | | Permanent-waved white hair | | |
|---|---|---|---|---|---|---|
| Examples | L* | a* | b* | L* | a* | b* |
| Example 1 | 35.9 | 33.3 | 16.9 | 33.1 | 33.4 | 16.4 |
| Example 2 | 22.5 | 22.7 | 1.0 | 18.2 | 17.1 | 1.9 |
| Example 3 | 33.9 | 32.9 | 15.1 | 30.8 | 31.2 | 14.9 |
| Example 4 | 20.9 | 21.2 | −0.2 | 17.6 | 14.6 | 1.24 |

The 4,5-diaminopyrazoles according to the invention thus make it possible to obtain strong and chromatic shades at alkaline pH.

Formulation Examples in Neutral Medium

The same formulations as above are prepared, replacing the aqueous ammonia with citric acid in an amount such that the pH of the composition is equal to 7 and starting with the bases and couplers below.

| Examples | Base | Coupler |
|---|---|---|
| 5 | 3-(4-,5 diaminopyrazol-1-yl)-propan-1-ol, HBr, HCl (5-1) | 2-methyl-5-aminophenol |
| 6 | 2-propyl-2H-pyrazol-3,4-diamine, HBr, HCl (5-2) | 2-methyl-5-aminophenol |

Locks of natural and permanent-waved gray hair containing 90% white hairs are dyed with the dye compositions 5 and 6 above in the same manner as for the dyeing at alkaline pH.

The following shades are obtained:

|          | Natural white hair | | | Permanent-waved white hair | | |
|----------|------|------|------|------|------|------|
| Examples | L*   | a*   | b*   | L*   | a*   | b*   |
| Example 5 | 39.5 | 31.6 | 26.7 | 32.8 | 33.8 | 25.7 |
| Example 6 | 37.3 | 25.6 | 19.7 | 29.9 | 28.7 | 19.7 |

At neutral pH, the 4,5-diaminopyrazoles according to the invention make it possible to obtain strong chromatic shades.

The invention claimed is:

1. A composition for the oxidation dyeing of keratin fibers, comprising, in a medium suitable for dyeing, at least one oxidation base chosen from diaminopyrazole compounds chosen from:

| Structure | Name |
|-----------|------|
| *(structure)* | 1-(4,5-diamino-pyrazol-1-yl)butane-2,3-diol |
| *(structure)* | 2-(4,5-diamino-pyrazol-1-yl)pentan-1-ol |
| *(structure)* | 4-(4,5-diamino-pyrazol-1-yl)butane-1,2-diol |
| *(structure)* | 4-(4,5-diamino-pyrazol-1-yl)pentan-2-ol |
| *(structure)* | 3-(4,5-diamino-pyrazol-1-yl)butane-1,2-diol |
| *(structure)* | 3-(4,5-diamino-pyrazol-1-yl)propane-1,2-diol |
| *(structure)* | 1-(4,5-diamino-pyrazol-1-yl)butane-2,4-diol |
| *(structure)* | 2-(4,5-diamino-pyrazol-1-yl)pentan-3-ol |

-continued

| Structure | Name |
|---|---|
| 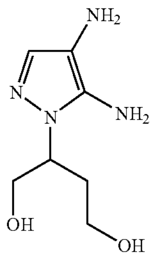 | 2-(4,5-diamino-pyrazol-1-yl)butane-1,4-diol |
| 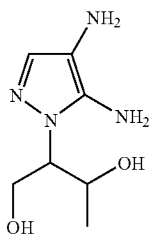 | 2-(4,5-diamino-pyrazol-1-yl)butane-1,3-diol |
| 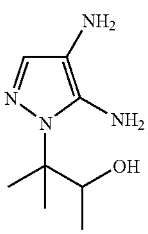 | 3-(4,5-diamino-pyrazol-1-yl)-3-methylbutan-2-ol |
| 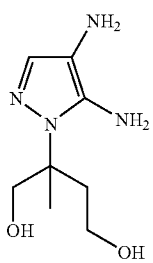 | 2-(4,5-diamino-pyrazol-1-yl)-2-methylbutane-1,4-diol |
| 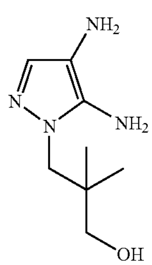 | 3-(4,5-diamino-pyrazol-1-yl)-2,2-dimethyl-propan-1-ol |
| 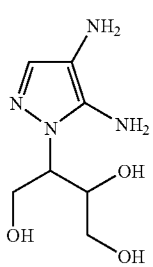 | 3-(4,5-diamino-pyrazol-1-yl)butane-1,2,4-triol |

-continued

| Structure | Name |
|---|---|
| 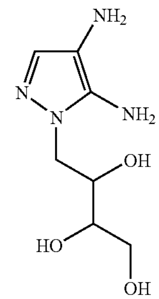 | 4-(4,5-diamino-pyrazol-1-yl)butane-1,2,3-triol |
| 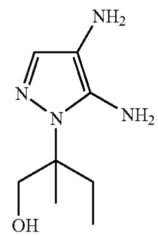 | 2-(4,5-diamino-pyrazol-1-yl)-2-methylbutan-1-ol |
| 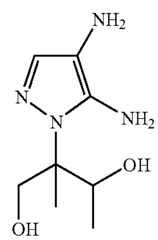 | 2-(4,5-diamino-pyrazol-1-yl)-2-methyl-pentane-1,3-diol |
| 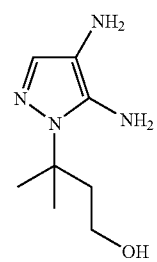 | 3-(4,5-diamino-pyrazol-1-yl)-3-methylbutan-1-ol |
| 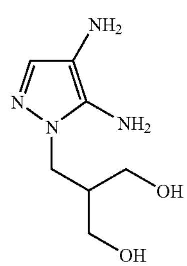 | 2-(4,5-diamino-pyrazol-1-ylmethyl)-propane-1,3-diol |
| 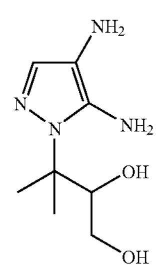 | 3-(4,5-diamino-pyrazol-1-yl)-3-methylbutane-1,2-diol |

| Structure | Name |
|---|---|
| 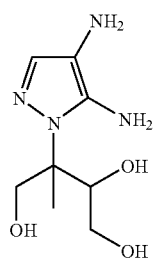 | 3-(4,5-diamino-pyrazol-1-yl)-3-methylbutane-1,2,4-triol |
| 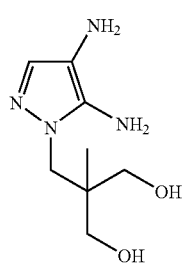 | 2-(4,5-diamino-pyrazol-1-ylmethyl)-2-methyl-propane-1,3-diol |
| 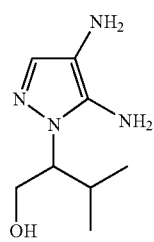 | 2-(4,5-diamino-pyrazol-1-yl)-3-methylbutan-1-ol |
| 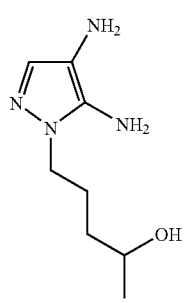 | 5-(4,5-diamino-pyrazol-1-yl)pentan-2-ol |
| 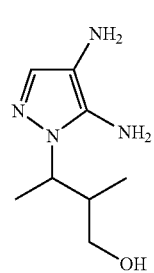 | 3-(4,5-diamino-pyrazol-1-yl)-2-methylbutan-1-ol |

| Structure | Name |
|---|---|
| 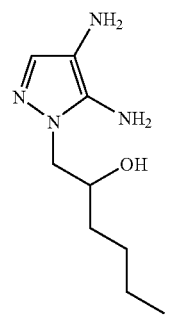 | 5-(4,5-diamino-pyrazol-1-yl)pentane-1,4-diol |
| 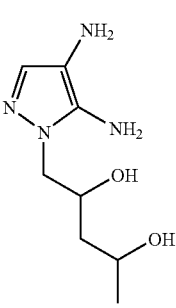 | 1-(4,5-diamino-pyrazol-1-yl)pentane-2,4-diol |
| 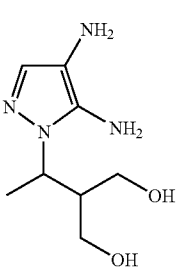 | 2-[1-(4,5-diamino-pyrazol-1-yl)ethyl]-propane-1,3-diol |
| 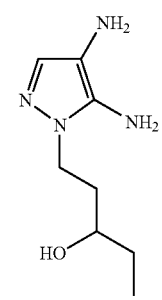 | 1-(4,5-diamino-pyrazol-1-yl)pentan-3-ol |
| 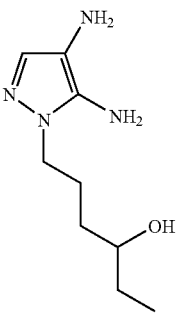 | 5-(4,5-diamino-pyrazol-1-yl)pentane-1,2-diol |

| Structure | Name |
|---|---|
| 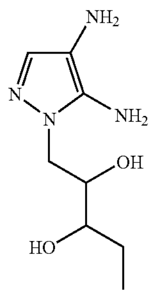 | 1-(4,5-diamino-pyrazol-1-yl)pentane-2,3-diol |
| 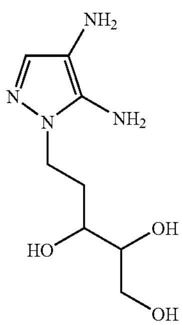 | 5-(4,5-diamino-pyrazol-1-yl)pentane-1,2,3-triol |
| 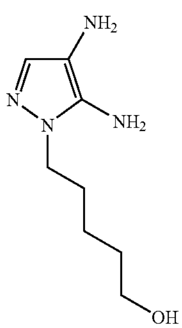 | 5-(4,5-diamino-pyrazol-1-yl)pentan-1-ol |
| 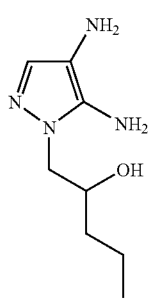 | 1-(4,5-diamino-pyrazol-1-yl)pentan-2-ol |
| 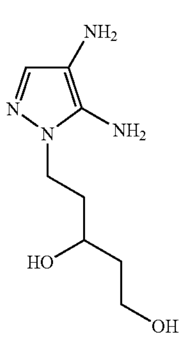 | 5-(4,5-diamino-pyrazol-1-yl)pentane-1,3-diol |

| Structure | Name |
|---|---|
| 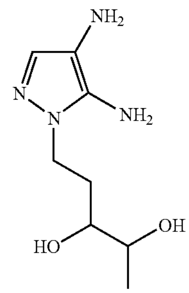 | 5-(4,5-diamino-pyrazol-1-yl)pentane-2,3-diol |
| 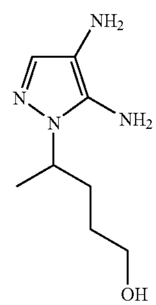 | 4-(4,5-diamino-pyrazol-1-yl)pentan-1-ol |
| 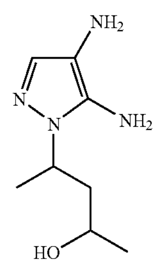 | 4-(4,5-diamino-pyrazol-1-yl)pentan-2-ol |
| 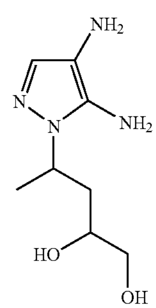 | 4-(4,5-diamino-pyrazol-1-yl)pentane-1,2-diol |
| 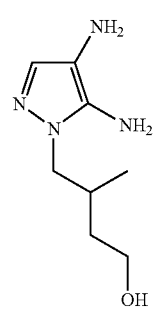 | 4-(4,5-diamino-pyrazol-1-yl)-3-methylbutan-1-ol |

| Structure | Name |
|---|---|
| 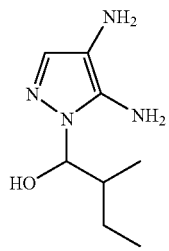 | 1-(4,5-diamino-pyrazol-1-yl)-2-methylbutan-1-ol |
| 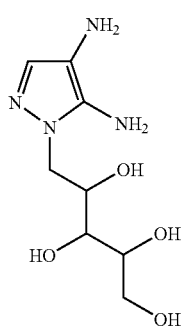 | 5-(4,5-diamino-pyrazol-1-yl)pentane-1,2,3,4-tetraol |
| 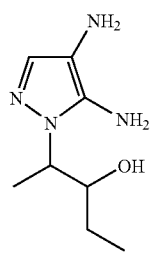 | 2-(4,5-diamino-pyrazol-1-yl)pentan-3-ol |
| 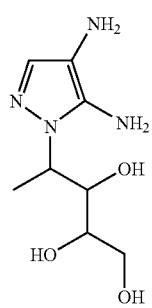 | 4-(4,5-diamino-pyrazol-1-yl)pentane-1,2,3-triol |
| 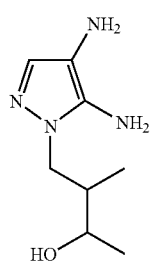 | 4-(4,5-diamino-pyrazol-1-yl)-3-methylbutan-2-ol |

| Structure | Name |
|---|---|
| 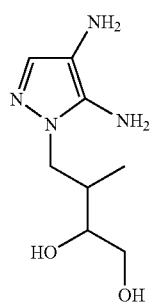 | 4-(4,5-diamino-pyrazol-1-yl)-3-methylbutane-1,2-diol |
| 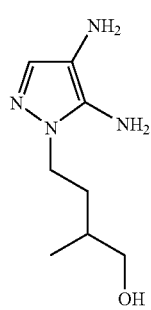 | 4-(4,5-diamino-pyrazol-1-yl)-2-methylbutan-1-ol |
| 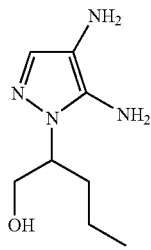 | 2-(4,5-diamino-pyrazol-1-yl)pentan-1-ol |
| 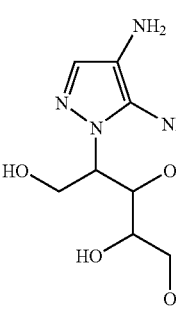 | 4-(4,5-diamino-pyrazol-1-yl)pentane-1,2,3,5-tetraol |
| 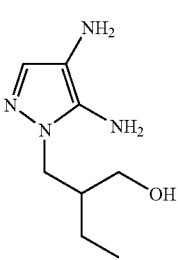 | 2-(4,5-diamino-pyrazol-1-ylmethyl)butan-1-ol |

-continued

| Structure | Name |
|---|---|
| 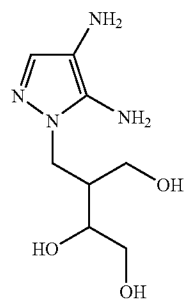 | 3-(4,5-diamino-pyrazol-1-ylmethyl)-butane-1,2,4-triol |
| 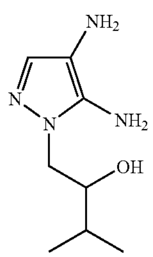 | 1-(4,5-diamino-pyrazol-1-yl)-3-methylbutan-2-ol |
| 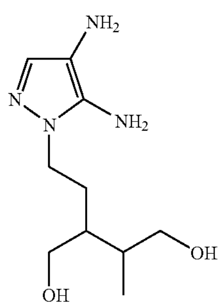 | 2-(4,5-diamino-pyrazol-1-yl)-3-methylbutane-1,4-diol |
| 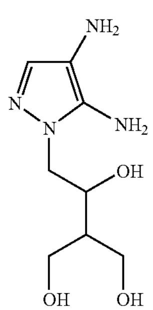 | 4-(4,5-diamino-pyrazol-1-yl)-2-hydroxymethyl-butane-1,3-diol |
| 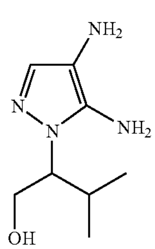 | 2-(4,5-diamino-pyrazol-1-yl)-3-methylbutan-1-ol |

-continued

| Structure | Name |
|---|---|
| 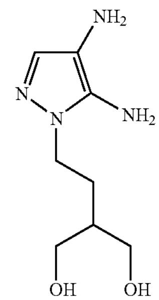 | 2-[2-(4,5-diamino-pyrazol-1-yl)ethyl]-propane-1,3-diol |
| 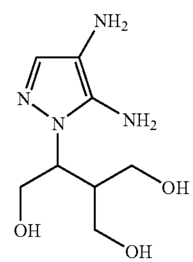 | 2-(4,5-diamino-pyrazol-1-yl)-3-hydroxymethyl-butane-1,4-diol |
| 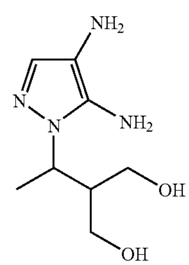 | 2-[1-(4,5-diamino-pyrazol-1-yl)ethyl]-propane-1,3-diol |
| 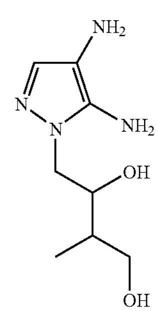 | 4-(4,5-diamino-pyrazol-1-yl)-2-methylbutane-1,3-diol |
| 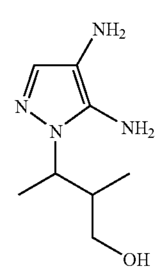 | 3-(4,5-diamino-pyrazol-1-yl)-2-methylbutan-1-ol |

| Structure | Name |
|---|---|
| | 2-(4,5-diamino-pyrazol-1-yl)-3-methylbutane-1,4-diol | and the physiologically acceptable acid addition salts thereof;

and at least one coupler chosen from 6-chloro-2-methyl-5-aminophenol, 3-aminophenol, 1,3-dihydroxy-2-methylbenzene, 4-chloro-1,3-dihydroxybenzene, 1,3-bis(2,4di-aminophenoxy)propane, 3-ureidoaniline, 3-ureido-1-di-methylaminobenzene, sesamol, 1-[β]-hydroxyethylamino-3,4-methylenedioxybenzene, [α]-naphthol, 2-methyl-1-naphthol, 6-hydroxyindole, 4-hydroxyindole, 4-hydroxy-N-methylindole, 2-amino-3-hydroypyridine, 6-hydroxybenzomorpholine, 3,5-diamino-2,6-dimethoxy-pyridine, 1-N-([β]-hydroxyethyl)amino-3,4-methylene-dioxybenzene and 2,6-bis([β]-hydroxyethylamino)toluene, and the addition salts thereof.

2. The composition according to claim 1, wherein the at least one diaminopyrazole compound is chosen from:

| Structure | Name |
|---|---|
| 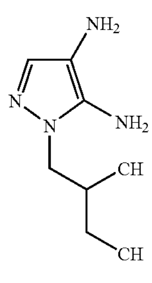 | 3-(4,5-diamino-pyrazol-1-yl)propane-1,2-diol |
| 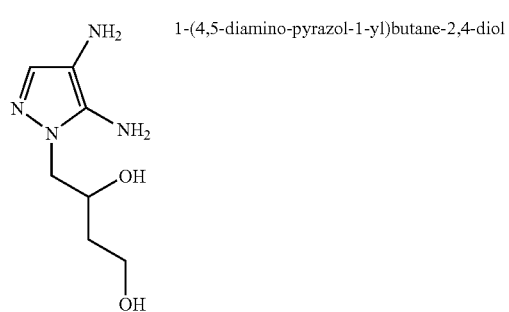 | 1-(4,5-diamino-pyrazol-1-yl)butane-2,4-diol |

| Structure | Name |
|---|---|
| 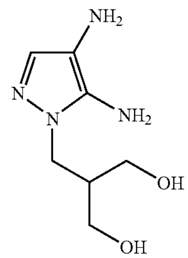 | 2-(4,5-diamino-pyrazol-1-ylmethyl)-propane-1,3-diol |
| 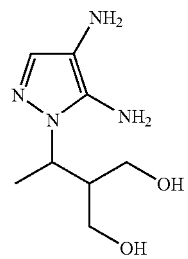 | 2-[1-(4,5-diamino-pyrazol-1-yl)ethyl]-propane-1,3-diol |
| 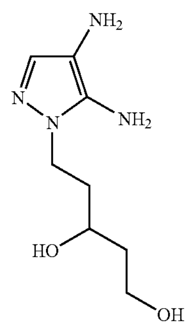 | 5-(4,5-diamino-pyrazol-1-yl)pentane-1,3-diol |
| 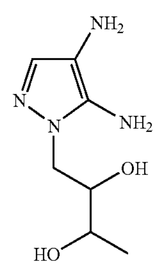 | 1-(4,5-diamino-pyrazol-1-yl)butane-2,3-diol |
| 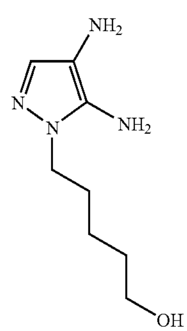 | 5-(4,5-diamino-pyrazol-1-yl)-pentan-1-ol |

-continued

| Structure | Name |
|---|---|
| 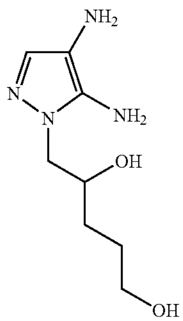 | 5-(4,5-diamino-pyrazol-1-yl)pentane-1,4-diol |
| 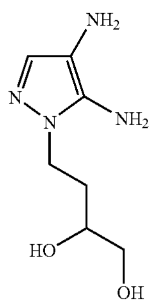 | 4-(4,5-diamino-pyrazol-1-yl)butane-1,2-diol |
| 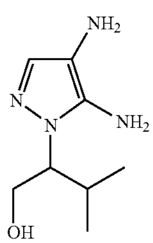 | 2-(4,5-diamino-pyrazol-1-yl)-3-methylbutan-1-ol |
| 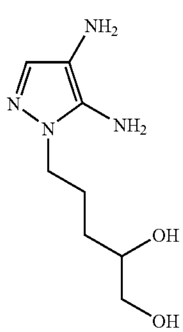 | 5-(4,5-diamino-pyrazol-1-yl)pentane-1,2-diol |
| 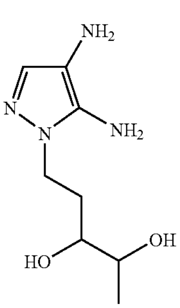 | 5-(4,5-diamino-pyrazol-1-yl)pentane-2,3-diol |

-continued

| Structure | Name |
|---|---|
| 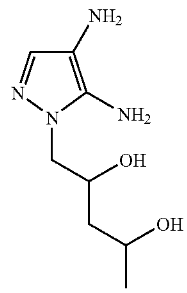 | 1-(4,5-diamino-pyrazol-1-yl)pentane-2,4-diol |
| 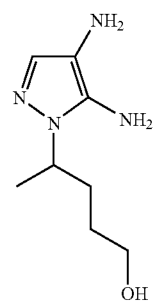 | 4-(4,5-diamino-pyrazol-1-yl)-pentan-1-ol |
| 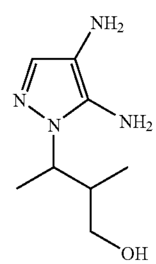 | 3-(4,5-diamino-pyrazol-1-yl)-2-methylbutan-1-ol |
| 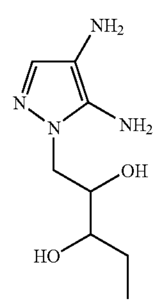 | 1-(4,5-diamino-pyrazol-1-yl)-pentane-2,3-diol |
| 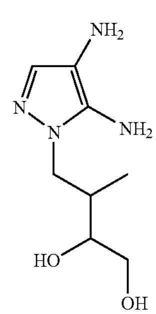 | 4-(4,5-diamino-pyrazol-1-yl)-3-methylbutane-1,2-diol |

| Structure | Name |
|---|---|
| (structure) | 2-[2-(4,5-diamino-pyrazol-1-yl)ethyl]-propane-1,3-diol | and the physiologically acceptable acid addition salts thereof.

3. The composition according to claim 2, wherein the at least one diaminopyrazole compound is chosen from:
3-(4,5-diaminopyrazol-1-yl)propane-1,2-diol
4-(4,5-diaminopyrazol-1-yl)butane-1,2-diol
5-(4,5-diaminopyrazol-1-yl)pentan-1-ol
and the physiologically acceptable acid addition salts thereof.

4. The composition according to claim 1, wherein said at least one oxidation base chosen from diaminopyrazole compounds as defined in claim 1, and physiologically acceptable salts thereof, is present in an amount ranging from 0.001% to 10% by weight relative to the total weight of the composition.

5. The composition according to claim 4, wherein said at least one oxidation base chosen from diaminopyrazole compounds, and physiologically acceptable salts thereof, is present in an amount ranging from 0.05% to 6% by weight relative to the total weight of the composition.

6. The composition according to claim 5, wherein said at least one oxidation base chosen from diaminopyrazole compounds, and physiologically acceptable salts thereof, is present in an amount ranging from 0.1% to 3% by weight relative to the total weight of the composition.

7. The composition according to claim 1, wherein said medium suitable for dyeing is chosen from water and mixtures of water and at least one organic solvent chosen from $C_1$-$C_4$ lower alkanols, polyols and polyol ethers, and aromatic alcohols.

8. The composition according to claim 1, said composition having a pH ranging from 3 to 12.

9. The composition according to claim 1, further comprising at least one additional oxidation base chosen from para-phenylendiamines, bis-(phenyl)alkylenediamines, para-aminophenols, ortho-aminophenols and heterocyclic bases other than the N-substituted diaminopyrazole as defined in claim 1, and acid addition salts thereof.

10. The composition according to claim 9, wherein said at least one additional oxidation base is present in an amount ranging from 0.0005% to 12% by weight relative to the total weight of the composition.

11. The composition according to claim 1, further comprising at least one additional coupler and/or at least one direct dye.

12. The composition according to claim 1, wherein said at least one additional coupler is chosen from meta-phenylendiamines, meta-aminophenols, meta-diphenols, mono- and polyhydroxylated naphthalene derivatives, heterocyclic couplers, and the acid addition salts thereof.

13. The composition according to claim 1, wherein said at least one coupler is present in an amount ranging from 0.0001% to 10% by weight, relative to the total weight of the composition.

14. The composition according to claim 1, wherein the physiologically acceptable salts are chosen from hydrochlorides, hydrobromides, sulfates, tartrates, lactates and acetates.

15. The composition according to claim 1, wherein said keratin fibers are human hair.

16. A process for dyeing keratin fibers, comprising applying to the keratin fibers a composition for the oxidation dyeing of keratin fibers, comprising, in a medium suitable for dyeing, at least one oxidation base, chosen from diaminopyrazole compounds chosen from:

| Structure | Name |
|---|---|
| (structure) | 3-(4,5-diamino-pyrazol-1-yl)propane-1,2-diol |
| (structure) | 1-(4,5-diamino-pyrazol-1-yl)butane-2,3-diol |
| (structure) | 2-(4,5-diamino-pyrazol-1-yl)pentan-1-ol |
| (structure) | 2-(4,5-diamino-pyrazol-1-yl)butane-1,3-diol |

-continued

| Structure | Name |
|---|---|
| 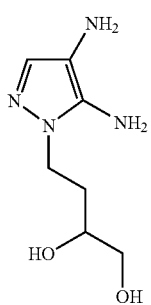 | 4-(4,5-diamino-pyrazol-1-yl)butane-1,2-diol |
| 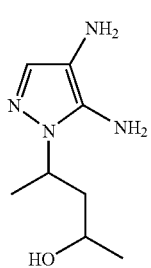 | 4-(4,5-diamino-pyrazol-1-yl)pentan-2-ol |
| 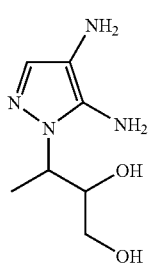 | 3-(4,5-diamino-pyrazol-1-yl)butane-1,2-diol |
| 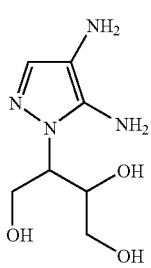 | 3-(4,5-diamino-pyrazol-1-yl)butane-1,2,4-triol |
| 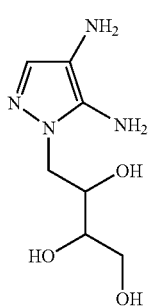 | 4-(4,5-diamino-pyrazol-1-yl)butane-1,2,3-triol |

-continued

| Structure | Name |
|---|---|
| 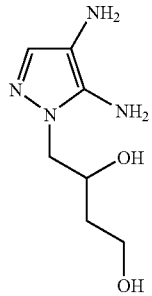 | 1-(4,5-diamino-pyrazol-1-yl)butane-2,4-diol |
| 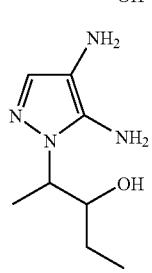 | 2-(4,5-diamino-pyrazol-1-yl)pentan-3-ol |
| 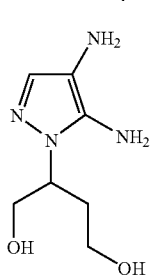 | 2-(4,5-diamino-pyrazol-1-yl)butane-1,4-diol |
| 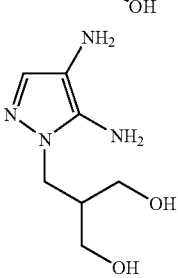 | 2-(4,5-diamino-pyrazol-1-ylmethyl)-propane-1,3-diol |
| 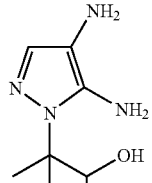 | 3-(4,5-diamino-pyrazol-1-yl)-3-methylbutan-2-ol |
| 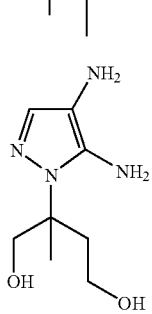 | 2-(4,5-diamino-pyrazol-1-yl)-2-methylbutane-1,4-diol |

-continued

| Structure | Name |
|---|---|
| 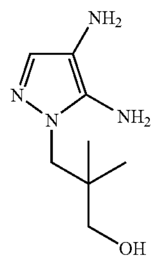 | 3-(4,5-diamino-pyrazol-1-yl)-2,2-dimethyl-propan-1-ol |
| 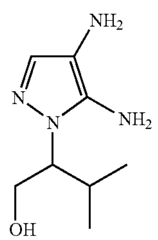 | 2-(4,5-diamino-pyrazol-1-yl)-3-methylbutan-1-ol |
| 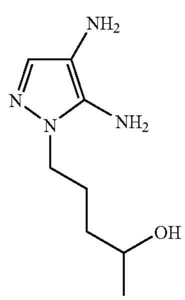 | 5-(4,5-diamino-pyrazol-1-yl)pentan-2-ol |
| 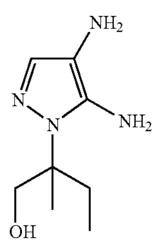 | 2-(4,5-diamino-pyrazol-1-yl)-2-methylbutan-1-ol |
| 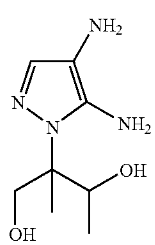 | 2-(4,5-diamino-pyrazol-1-yl)-2-methyl-pentane-1,3-diol |
| 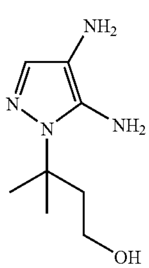 | 3-(4,5-diamino-pyrazol-1-yl)-3-methylbutan-1-ol |

-continued

| Structure | Name |
|---|---|
| 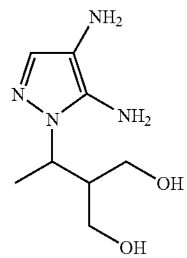 | 2-[1-(4,5-diamino-pyrazol-1-yl)ethyl]-propane-1,3-diol |
| 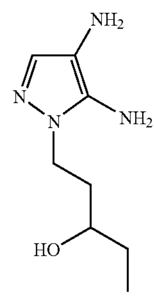 | 1-(4,5-diamino-pyrazol-1-yl)pentan-3-ol |
| 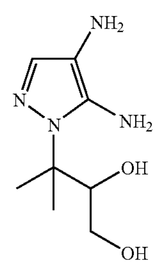 | 3-(4,5-diamino-pyrazol-1-yl)-3-methylbutane-1,2-diol |
| 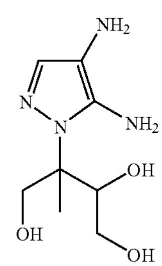 | 3-(4,5-diamino-pyrazol-1-yl)-3-methylbutane-1,2,4-triol |
| 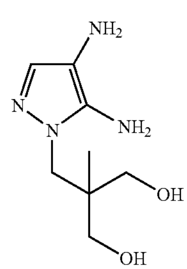 | 2-(4,5-diamino-pyrazol-1-ylmethyl)-2-methyl-propane-1,3-diol |

| Structure | Name |
|---|---|
| 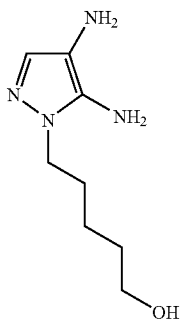 | 5-(4,5-diamino-pyrazol-1-yl)pentan-1-ol |
| 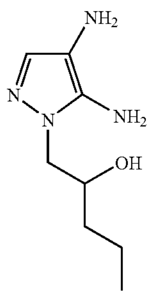 | 1-(4,5-diamino-pyrazol-1-yl)pentan-2-ol |
| 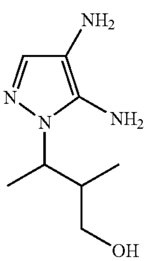 | 3-(4,5-diamino-pyrazol-1-yl)-2-methylbutan-1-ol |
| 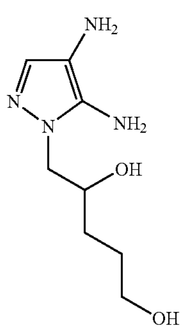 | 5-(4,5-diamino-pyrazol-1-yl)pentane-1,4-diol |
| 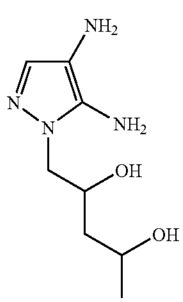 | 1-(4,5-diamino-pyrazol-1-yl)pentane-2,4-diol |
| | 4-(4,5-diamino-pyrazol-1-yl)pentan-2-ol |
| | 4-(4,5-diamino-pyrazol-1-yl)pentane-1,2-diol |
| | 5-(4,5-diamino-pyrazol-1-yl)pentane-1,2-diol |
| | 1-(4,5-diamino-pyrazol-1-yl)pentane-2,3-diol |
| | 5-(4,5-diamino-pyrazol-1-yl)pentane-1,2,3-triol |

| Structure | Name |
|---|---|
| 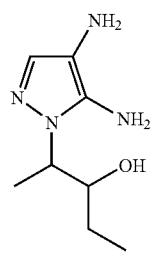 | 2-(4,5-diamino-pyrazol-1-yl)pentan-3-ol |
| 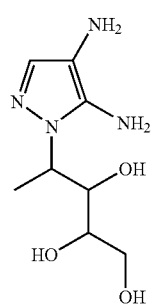 | 4-(4,5-diamino-pyrazol-1-yl)pentane-1,2,3-triol |
| 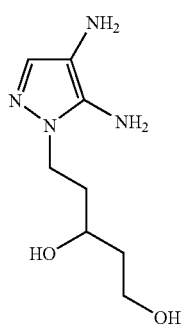 | 5-(4,5-diamino-pyrazol-1-yl)pentane-1,3-diol |
| 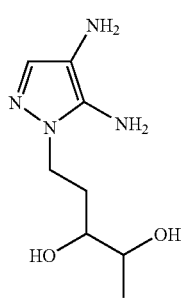 | 5-(4,5-diamino-pyrazol-1-yl)pentane-2,3-diol |
| 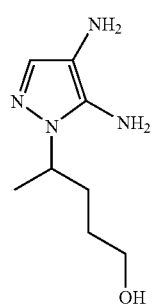 | 4-(4,5-diamino-pyrazol-1-yl)pentan-1-ol |
| 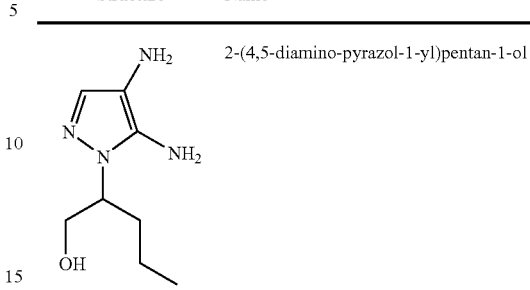 | 2-(4,5-diamino-pyrazol-1-yl)pentan-1-ol |
| 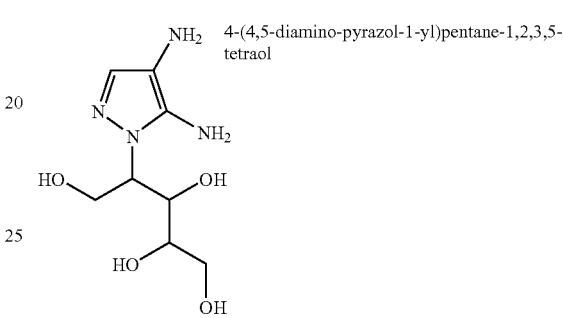 | 4-(4,5-diamino-pyrazol-1-yl)pentane-1,2,3,5-tetraol |
| 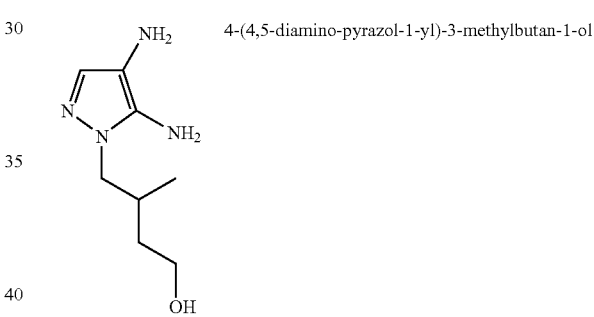 | 4-(4,5-diamino-pyrazol-1-yl)-3-methylbutan-1-ol |
| 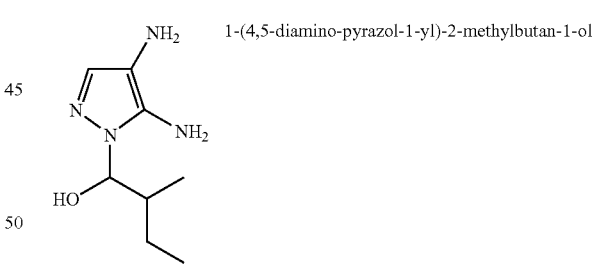 | 1-(4,5-diamino-pyrazol-1-yl)-2-methylbutan-1-ol |
| 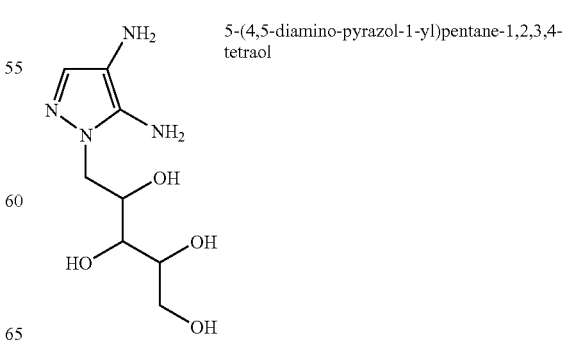 | 5-(4,5-diamino-pyrazol-1-yl)pentane-1,2,3,4-tetraol |

-continued

| Structure | Name |
|---|---|
| 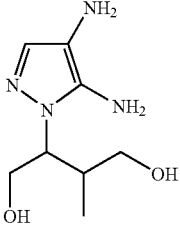 | 2-(4,5-diamino-pyrazol-1-yl)-3-methylbutane-1,4-diol |
| 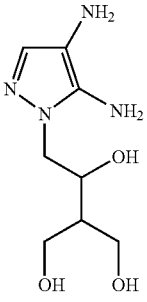 | 4-(4,5-diamino-pyrazol-1-yl)-2-hydroxymethyl-butane-1,3-diol |
| 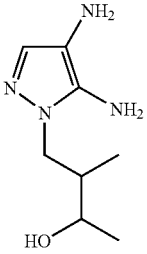 | 4-(4,5-diamino-pyrazol-1-yl)-3-methylbutan-2-ol |
| 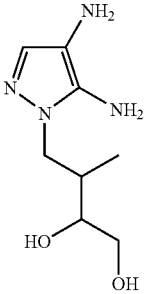 | 4-(4,5-diamino-pyrazol-1-yl)-3-methylbutane-1,2-diol |
| 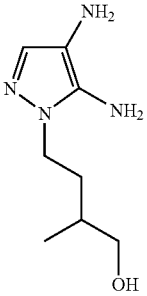 | 4-(4,5-diamino-pyrazol-1-yl)-2-methylbutan-1-ol |

-continued

| Structure | Name |
|---|---|
| 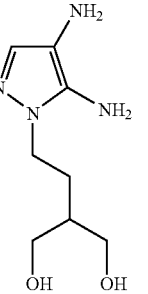 | 2-[2-(4,5-diamino-pyrazol-1-yl)ethyl]-propane-1,3-diol |
| 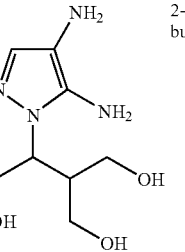 | 2-(4,5-diamino-pyrazol-1-yl)-3-hydroxymethyl-butane-1,4-diol |
| 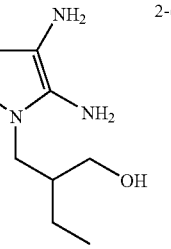 | 2-(4,5-diamino-pyrazol-1-ylmethyl)butan-1-ol |
| 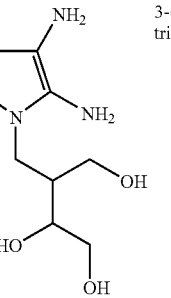 | 3-(4,5-diamino-pyrazol-1-ylmethyl)-butane-1,2,4-triol |
| 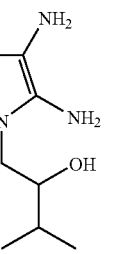 | 1-(4,5-diamino-pyrazol-1-yl)-3-methylbutan-2-ol |

-continued

| Structure | Name |
|---|---|
| 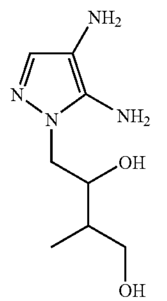 | 4-(4,5-diamino-pyrazol-1-yl)-2-methylbutane-1,3-diol |
| 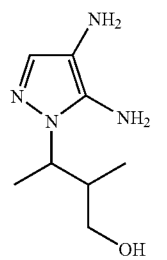 | 3-(4,5-diamino-pyrazol-1-yl)-2-methylbutan-1-ol |
| 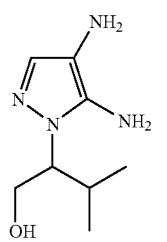 | 2-(4,5-diamino-pyrazol-1-yl)-3-methylbutan-1-ol |
| 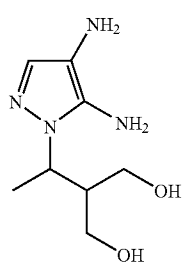 | 2-[1-(4,5-diamino-pyrazol-1-yl)ethyl]-propane-1,3-diol |
| | 2-(4,5-diamino-pyrazol-1-yl)-3-methylbutane-1,4-diol | and the physiologically acceptable acid addition salts thereof, and at least one coupler chosen from 6-chloro-2-methyl-5-aminophenol, 3-aminophenol, 1,3-dihydroxy-2-methylbenzene, 4-chloro-1,3-dihydroxybenzene, 1,3-bis(2,4-di-aminophenoxy)propane, 3-ureidoaniline, 3-ureido-1-di-methylaminobenzene, sesamol, 1-[β]-hydroxyethylamino-3,4-methylenedioxybenzene, [α]-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxy-pyridine, 1-N-([β]-hydroxyethyl)amino-3,4-methylene-dioxybenzene and 2,6-bis([β]-hydroxyethylamino)toluene, and the addition salts thereof, wherein said composition is applied to the fibers for a period of time that is sufficient to develop the desired color, either in air or using an oxidizing agent.

17. The process according to claim 16, wherein the at least one diaminopyrazole compound is chosen from:

| Structure | Name |
|---|---|
| 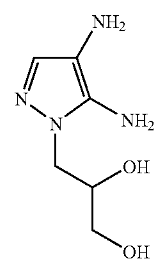 | 3-(4,5-diamino-pyrazol-1-yl)propane-1,2-diol |
| 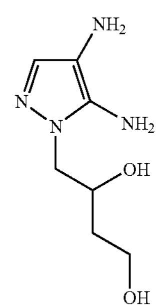 | 1-(4,5-diamino-pyrazol-1-yl)butane-2,4-diol |
| 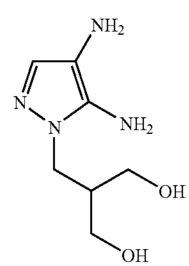 | 2-(4,5-diamino-pyrazol-1-ylmethyl)-propane-1,3-diol |
| 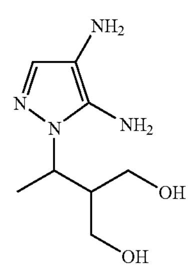 | 2-[1-(4,5-diamino-pyrazol-1-yl)ethyl]-propane-1,3-diol |

-continued

| Structure | Name |
|---|---|
| 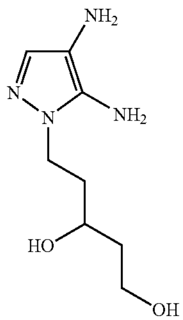 | 5-(4,5-diamino-pyrazol-1-yl)pentane-1,3-diol |
| 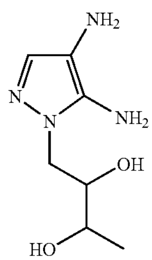 | 1-(4,5-diamino-pyrazol-1-yl)butane-2,3-diol |
| 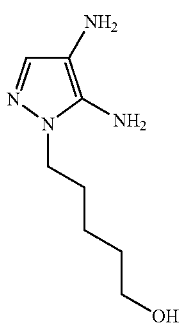 | 5-(4,5-diamino-pyrazol-1-yl)-pentan-1-ol |
| 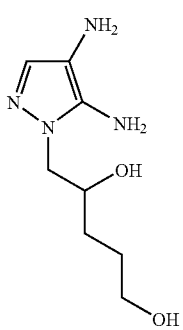 | 5-(4,5-diamino-pyrazol-1-yl)pentane-1,4-diol |
| 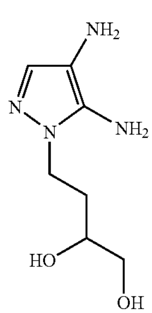 | 4-(4,5-diamino-pyrazol-1-yl)butane-1,2-diol |

-continued

| Structure | Name |
|---|---|
| 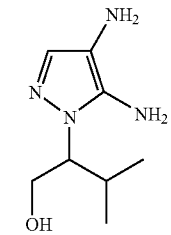 | 2-(4,5-diamino-pyrazol-1-yl)-3-methylbutan-1-ol |
| 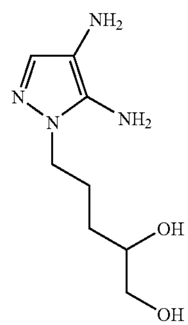 | 5-(4,5-diamino-pyrazol-1-yl)pentane-1,2-diol |
| 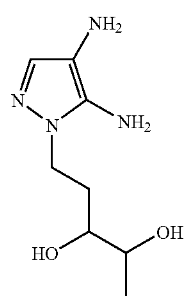 | 5-(4,5-diamino-pyrazol-1-yl)pentane-2,3-diol |
| 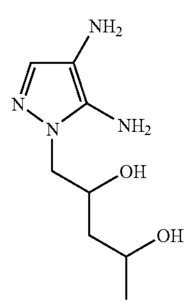 | 1-(4,5-diamino-pyrazol-1-yl)pentane-2,4-diol |
| 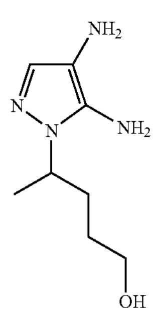 | 4-(4,5-diamino-pyrazol-1-yl)pentan-1-ol |

-continued

| Structure | Name |
|---|---|
| 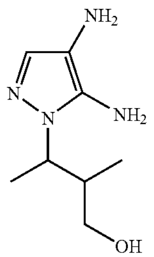 | 3-(4,5-diamino-pyrazol-1-yl)-2-methylbutan-1-ol |
| 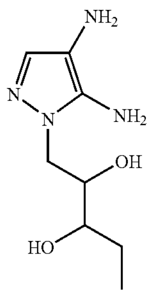 | 1-(4,5-diamino-pyrazol-1-yl)-pentane-2,3-diol |
| 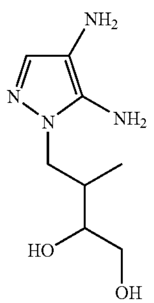 | 4-(4,5-diamino-pyrazol-1-yl)-3-methylbutane-1,2-diol |
| | 2-[2-(4,5-diamino-pyrazol-1-yl)ethyl]-propane-1,3-diol | and the physiologically acceptable acid addition salts thereof.

18. The process according to claim 17, wherein the at least one diaminopyrazole compound is chosen from:

3-(4,5-diaminopyrazol-1-yl)propane-1,2-diol
4-(4,5-diaminopyrazol-1-yl)butane-1,2-diol
5-(4,5-diaminopyrazol-1-yl)pentan-1-ol and the physiologically acceptable acid addition salts thereof.

19. The process according to claim 16, wherein said composition is applied to the keratin fibers in the presence of at least one oxidation catalyst.

20. The process according to claim 16, wherein said color is revealed on contact with atmospheric oxygen.

21. The process according to claim 16, wherein said color is revealed at acidic, neutral or alkaline pH with the aid of an oxidizing agent, which is added to the dye composition at the time of use, or which is present in an oxidizing composition applied simultaneously or sequentially in a separate manner.

22. The process according to claim 16, wherein said at least one oxidizing agent is chosen from hydrogen peroxide, urea peroxide, alkali metal bromates, and persalts.

23. A process according to claim 22, wherein said persalts are chosen from perborates and persulfates.

24. The process according to claim 16, wherein the composition for oxidation dyeing further comprises at least one additional coupler.

25. A process according to claim 16, wherein said keratin fibers are human hair.

26. A multi-compartment device comprising:
a first compartment containing a composition for the oxidation dyeing of keratin fibers, comprising, in a medium suitable for dyeing, at least one as oxidation base, chosen from diaminopyrazole compounds chosen from:

| Structure | Name |
|---|---|
| 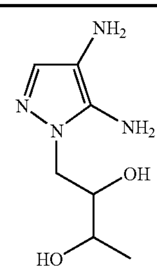 | 1-(4,5-diamino-pyrazol-1-yl)butane-2,3-diol |
| 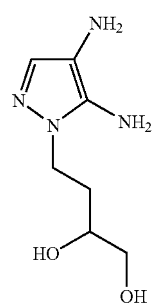 | 4-(4,5-diamino-pyrazol-1-yl)butane-1,2-diol |
| 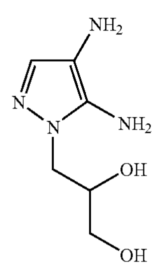 | 3-(4,5-diamino-pyrazol-1-yl)propane-1,2-diol |

| Structure | Name |
|---|---|
| 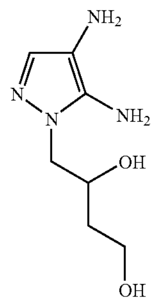 | 1-(4,5-diamino-pyrazol-1-yl)butane-2,4-diol |
| 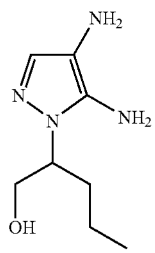 | 2-(4,5-diamino-pyrazol-1-yl)pentan-1-ol |
| 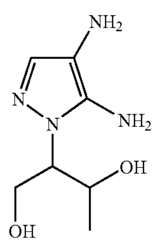 | 2-(4,5-diamino-pyrazol-1-yl)butane-1,3-diol |
| 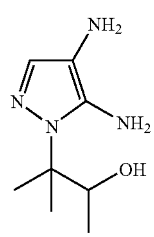 | 3-(4,5-diamino-pyrazol-1-yl)-3-methylbutan-2-ol |
| 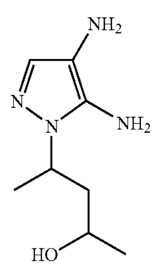 | 4-(4,5-diamino-pyrazol-1-yl)pentan-2-ol |
| 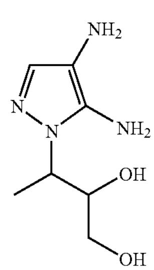 | 3-(4,5-diamino-pyrazol-1-yl)butane-1,2-diol |
| | 3-(4,5-diamino-pyrazol-1-yl)butane-1,2,4-triol |
| | 4-(4,5-diamino-pyrazol-1-yl)butane-1,2,3-triol |
| | 2-(4,5-diamino-pyrazol-1-yl)-2-methylbutan-1-ol |
| | 2-(4,5-diamino-pyrazol-1-yl)pentan-3-ol |
| | 2-(4,5-diamino-pyrazol-1-yl)butane-1,4-diol |
| | 2-(4,5-diamino-pyrazol-1-ylmethyl)-propane-1,3-diol |

-continued

| Structure | Name |
|---|---|
| 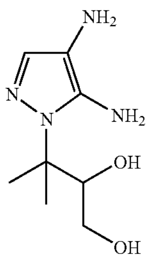 | 3-(4,5-diamino-pyrazol-1-yl)-3-methylbutane-1,2-diol |
| 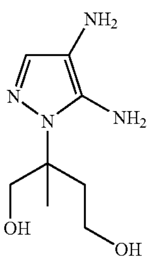 | 2-(4,5-diamino-pyrazol-1-yl)-2-methylbutane-1,4-diol |
| 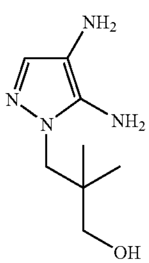 | 3-(4,5-diamino-pyrazol-1-yl)-2,2-dimethyl-propan-1-ol |
| 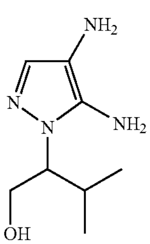 | 2-(4,5-diamino-pyrazol-1-yl)-3-methylbutan-1-ol |
| 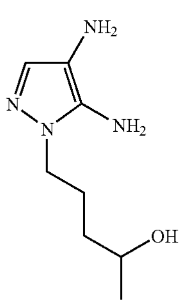 | 5-(4,5-diamino-pyrazol-1-yl)pentan-2-ol |

-continued

| Structure | Name |
|---|---|
| 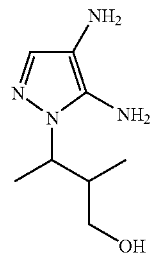 | 3-(4,5-diamino-pyrazol-1-yl)-2-methylbutan-1-ol |
| 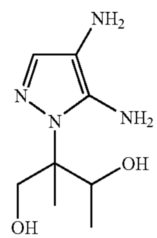 | 2-(4,5-diamino-pyrazol-1-yl)-2-methyl-pentane-1,3-diol |
| 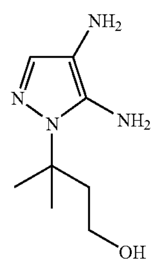 | 3-(4,5-diamino-pyrazol-1-yl)-3-methylbutan-1-ol |
| 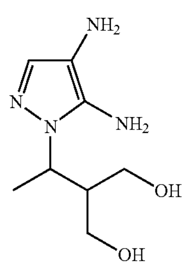 | 2-[1-(4,5-diamino-pyrazol-1-yl)ethyl]-propane-1,3-diol |
| 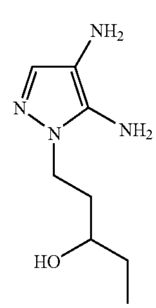 | 1-(4,5-diamino-pyrazol-1-yl)pentan-3-ol |

-continued

| Structure | Name |
|---|---|
| 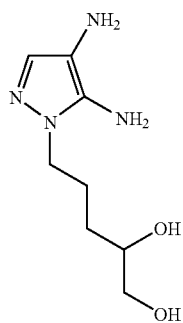 | 5-(4,5-diamino-pyrazol-1-yl)pentane-1,2-diol |
| 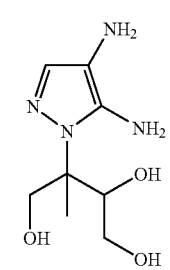 | 3-(4,5-diamino-pyrazol-1-yl)-3-methylbutane-1,2,4-triol |
| 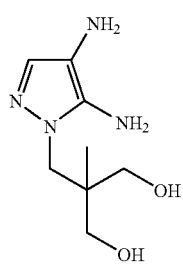 | 2-(4,5-diamino-pyrazol-1-ylmethyl)-2-methyl-propane-1,3-diol |
| 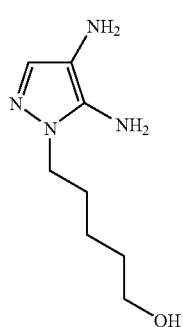 | 5-(4,5-diamino-pyrazol-1-yl)pentan-1-ol |
| 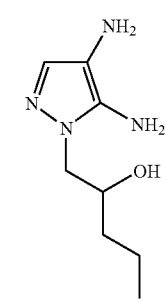 | 1-(4,5-diamino-pyrazol-1-yl)pentan-2-ol |

-continued

| Structure | Name |
|---|---|
| 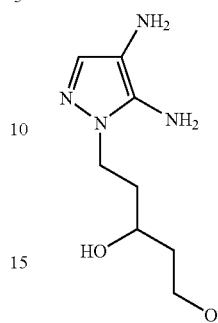 | 5-(4,5-diamino-pyrazol-1-yl)pentane-1,3-diol |
| 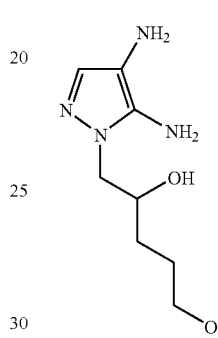 | 5-(4,5-diamino-pyrazol-1-yl)pentane-1,4-diol |
| 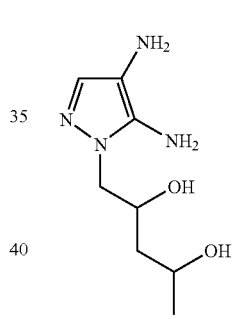 | 1-(4,5-diamino-pyrazol-1-yl)pentane-2,4-diol |
| 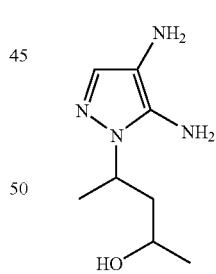 | 4-(4,5-diamino-pyrazol-1-yl)pentan-2-ol |
| 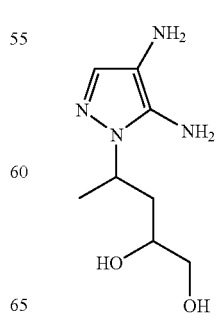 | 4-(4,5-diamino-pyrazol-1-yl)pentane-1,2-diol |

-continued

| Structure | Name |
|---|---|
| 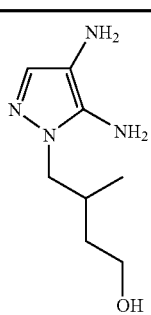 | 4-(4,5-diamino-pyrazol-1-yl)-3-methylbutan-1-ol |
| 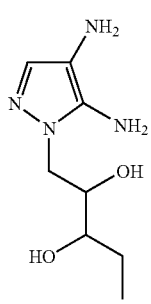 | 1-(4,5-diamino-pyrazol-1-yl)pentane-2,3-diol |
| 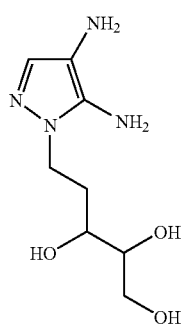 | 5-(4,5-diamino-pyrazol-1-yl)pentane-1,2,3-triol |
| 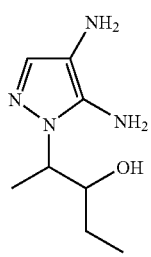 | 2-(4,5-diamino-pyrazol-1-yl)pentan-3-ol |
| 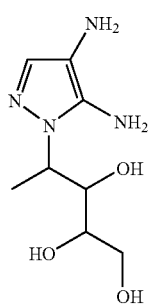 | 4-(4,5-diamino-pyrazol-1-yl)pentane-1,2,3-triol |

-continued

| Structure | Name |
|---|---|
| 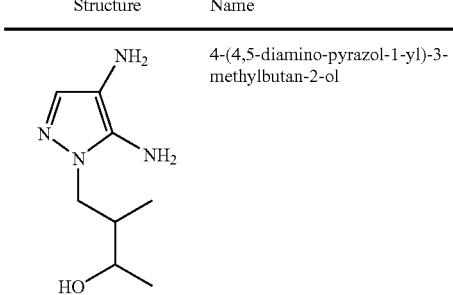 | 4-(4,5-diamino-pyrazol-1-yl)-3-methylbutan-2-ol |
| 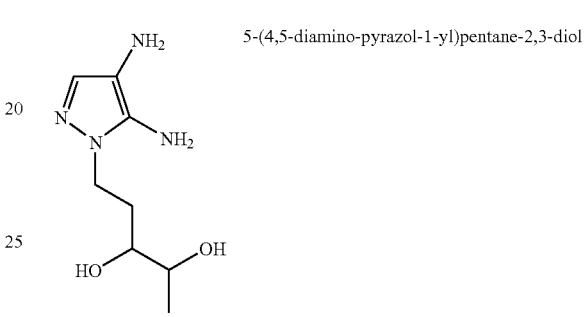 | 5-(4,5-diamino-pyrazol-1-yl)pentane-2,3-diol |
| 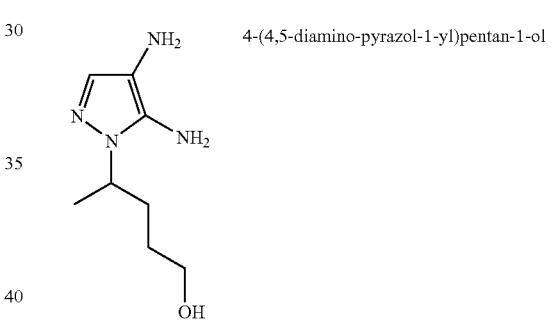 | 4-(4,5-diamino-pyrazol-1-yl)pentan-1-ol |
| 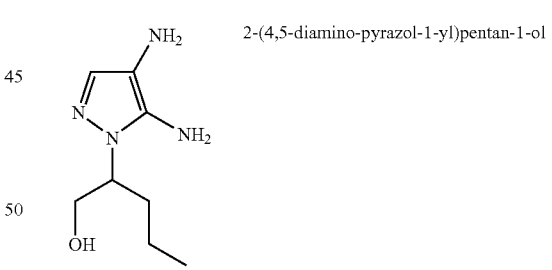 | 2-(4,5-diamino-pyrazol-1-yl)pentan-1-ol |
| 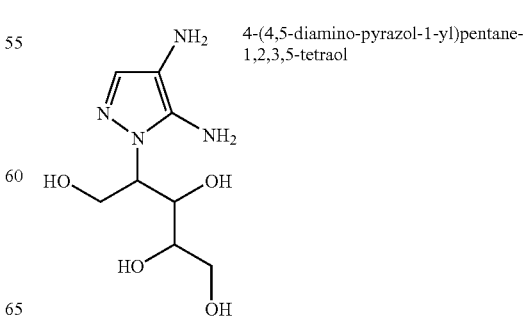 | 4-(4,5-diamino-pyrazol-1-yl)pentane-1,2,3,5-tetraol |

| Structure | Name |
|---|---|
| 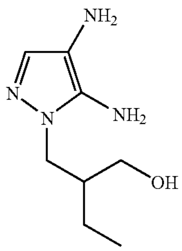 | 2-(4,5-diamino-pyrazol-1-ylmethylbutan-1-ol |
| 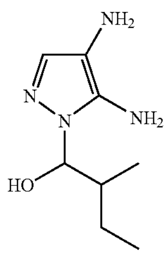 | 1-(4,5-diamino-pyrazol-1-yl)-2-methylbutan-1-ol |
| 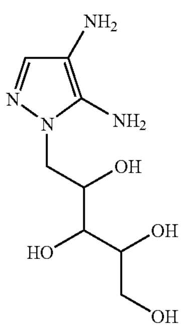 | 5-(4,5-diamino-pyrazol-1-yl)pentane-1,2,3,4-tetraol |
| 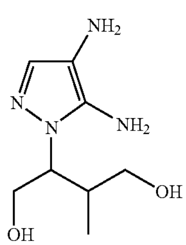 | 2-(4,5-diamino-pyrazol-1-yl)-3-methylbutane-1,4-diol |
| 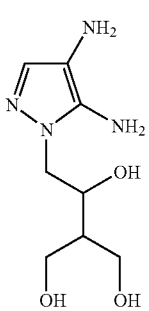 | 4-(4,5-diamino-pyrazol-1-yl)-2-hydroxymethyl-butane-1,3-diol |
| | 2-(4,5-diamino-pyrazol-1-yl)-3-methylbutan-1-ol |
| | 4-(4,5-diamino-pyrazol-1-yl)-3-methylbutane-1,2-diol |
| | 4-(4,5-diamino-pyrazol-1-yl)-2-methylbutan-1-ol |
| | 2-[2-(4,5-diamino-pyrazol-1-yl)ethyl]-propane-1,3-diol |
| | 2-(4,5-diamino-pyrazol-1-yl)-3-hydroxymethyl-butane-1,4-diol |

-continued

| Structure | Name |
|---|---|
| 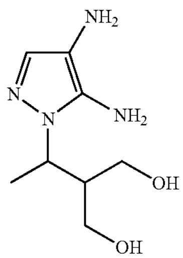 | 2-[1-(4,5-diamino-pyrazol-1-yl)ethyl]-propane-1,3-diol |
| 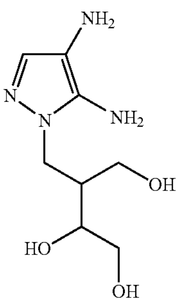 | 3-(4,5-diamino-pyrazol-1-ylmethyl)-butane-1,2,4-triol |
| 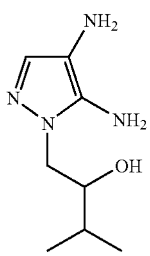 | 1,(4,5-diamino-pyrazol-1-yl)-3-methylbutan-2-ol |

-continued

| Structure | Name |
|---|---|
| 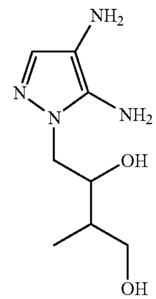 | 4-(4,5-diamino-pyrazol-1-yl)-2-methylbutane-1,3-diol |
| 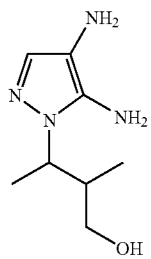 | 3-(4,5-diamino-pyrazol-1-yl)-2-methylbutan-1-ol |
| | 2-(4,5-diamino-pyrazol-1-yl)-3-methylbutane-1,4-diol | and the physiologically acceptable acid salts thereof;
and a second compartment containing an oxidizing composition.

* * * * *

UNITED STATES PATENT AND TRADEMARK OFFICE
CERTIFICATE OF CORRECTION

PATENT NO.        : 7,285,136 B2                                          Page 1 of 1
APPLICATION NO. : 10/468288
DATED             : October 23, 2007
INVENTOR(S)       : Thilo Fessman et al.

It is certified that error appears in the above-identified patent and that said Letters Patent is hereby corrected as shown below:

Claim 2, col. 41, lines 42-54:

" 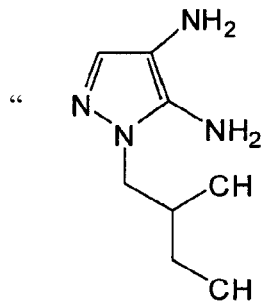  " should read -- 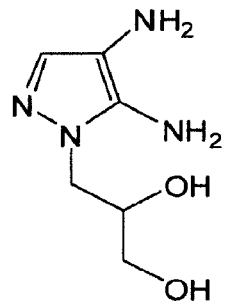 --

Signed and Sealed this

Twenty Second Day of April, 2008

JON W. DUDAS
*Director of the United States Patent and Trademark Office*